US007108865B2

(12) United States Patent
Curatolo et al.

(10) Patent No.: US 7,108,865 B2
(45) Date of Patent: Sep. 19, 2006

(54) CONTROLLED-RELEASE DOSAGE FORMS OF AZITHROMYCIN

(75) Inventors: William J. Curatolo, Niantic, CT (US); Hylar L. Friedman, Brattleboro, VT (US); Richard W. Korsmeyer, Old Lyme, CT (US); Steven R. LeMott, East Lyme, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/803,628

(22) Filed: Mar. 9, 2001

(65) Prior Publication Data
US 2002/0044965 A1    Apr. 18, 2002

Related U.S. Application Data

(60) Continuation of application No. 09/577,059, filed on May 22, 2000, which is a division of application No. 08/727,634, filed as application No. PCT/IB95/00264 on Apr. 13, 1995, now Pat. No. 6,068,859, which is a continuation-in-part of application No. 08/239,094, filed on May 6, 1994, now abandoned.

(51) Int. Cl.
A61K 9/14    (2006.01)
(52) U.S. Cl. .................. 424/489; 424/400; 424/464; 424/468; 424/469; 424/489; 424/490; 514/29; 514/964
(58) Field of Classification Search ........... 424/469, 424/488, 490, 400, 464, 468, 489; 514/28, 514/29, 964
See application file for complete search history.

(56) References Cited

U.S. PATENT DOCUMENTS

| 4,434,153 | A | * | 2/1984 | Urquhart et al. ............... 424/22 |
| 4,474,768 | A | | 10/1984 | Bright |
| 4,517,359 | A | | 5/1985 | Kobrehel et al. |
| 4,522,625 | A | | 6/1985 | Edgre |
| 4,755,385 | A | | 7/1988 | Etienne et al. ............... 424/154 |
| 4,792,448 | A | | 12/1988 | Ranade |
| 4,851,231 | A | * | 7/1989 | Urquhart et al. ............ 424/469 |
| 4,963,531 | A | | 10/1990 | Remington |
| 4,968,507 | A | | 11/1990 | Zentner et al. |
| 5,114,718 | A | | 5/1992 | Damani ............... 424/422 |
| 5,173,299 | A | | 12/1992 | Damani ............... 424/435 |
| 5,198,220 | A | | 3/1993 | Damani ............... 424/426 |
| 5,230,895 | A | | 7/1993 | Czarnecki et al. ......... 424/422 |
| 5,605,889 | A | * | 2/1997 | Curatolo et al. ............. 514/29 |
| 5,705,190 | A | | 1/1998 | Broad et al. |
| 5,747,058 | A | | 5/1998 | Tipton et al. |
| 6,068,859 | A | | 5/2000 | Curatolo et al. ............ 424/490 |

FOREIGN PATENT DOCUMENTS

| EP | 0080341 | 7/1983 |
| EP | 0128655 | 12/1984 |
| EP | 0109253 | 10/1987 |
| EP | 0243302 | 10/1987 |
| EP | 0298650 | 1/1989 |
| EP | 0302836 | 2/1989 |
| EP | 0307128 | 3/1989 |
| EP | 0378404 | 7/1990 |
| EP | 0429225 | 5/1991 |
| EP | 0430474 | 6/1991 |
| EP | 0582396 | 2/1994 |
| EP | 0679400 | 11/1995 |
| GB | 2066070 | 7/1981 |
| GB | 2091097 | 7/1982 |
| WO | 8902271 | 3/1989 |
| WO | 9009168 | 8/1990 |
| WO | 9101131 | 2/1991 |
| WO | 9117744 | 11/1991 |
| WO | WO 9204890 | 4/1992 |
| WO | 9400112 | 1/1994 |
| WO | 9412159 | 6/1994 |
| WO | 9509601 | 4/1995 |

OTHER PUBLICATIONS

Morishita et al., Controlled Release Microspheres Based on Eudragit L100 for the Oral Administration of Erythromycin, 1991, Drug, Design and Delivery, vol. 7, pp. 309-319.*
Martindale, The Extra Pharmacopoiea, 30th, The Pharm. Press, London, 1963, p. 1197.
PDR, 48th, Med. L994, N.Y. p. 1789.
The Merck Index, 11th, Merck & Co., N.Y., 1989, p. 146 Remington Pharmaceutical Science, 16th Merck Pub.
Farmacia Practica de Remington, second Spanish edition, UTEHA, Mexico, 1965, pp. 471 and 525.
Laegemiddelkataloget, Copenhagen 1992, p. 229, and p. 356.
Farmaceuten, No. 12, 1990, p. 402-405.
Hon-Leung Lee et al., "Drug Properties Influencing The Design of Sustained or Controlled Release Drug Delivery".
Chapters 88, 90, and 91 from Remington Pharmaceutical Science, 16th Merck Pub., Co., Pennsylvania (1980), pp. 1535, 1585, 1594.
Scott Hopkins, The American Journal of Medicine, vol. 91, (Suppl 3A) Sep. 12, 1991, 3A-40S-3A-45S.
J. R. Cardinal, Plenum Publishing Corp., 1984, Drug Release From Matrix Devices.
Richard H. Drew, Pharmacotherapy, vol. 12, No. 3, 1992, pp. 162-173.

(Continued)

Primary Examiner—Shelly A. Dodson
Assistant Examiner—Konata M. George
(74) Attorney, Agent, or Firm—Gregg C. Benson; James T. Jones

(57) ABSTRACT

A controlled-release dosage form of azithromycin having an improved side effect profile; a process for preparing the dosage form; and a method of treating a microbial infection, comprising administering azithromycin in such a controlled-release dosage form to a mammal, including a human patient, in need of such treatment.

28 Claims, 1 Drawing Sheet

OTHER PUBLICATIONS

Chem. Abstr., Yoshitomi, H., et al., V 119, No. 8, p. 496, abst. No. 79946v, "Evaluation of Enteric Coated Tablet Sensitive to Pancreatic Lipase I. In Vitro Disintegration Test".

Farmaceitisk Tidente, No. 35/36, 1988, p. 537-548.

Milap C. Nahata et al., Antimicrobial Agents and Chemotherapy, vol. 37/2, Feb. 1993, pp. 314-316.

Gazzetta Ufficiale Della Repubblica Italiana, No. 103 of May 5, 1992 along with English translation.

H. Sucker, et al, Pharmazeutische Technologie, 2nd Edition 1991, Sections 4.4.1 to 4.4.3 along with English translation.

Physician's Desk Reference, 47th Ed. 1993, entry zithromax.

H. N. Nellans, et al., Abstract 518, 31st Interscience Conf. on Antimicrobial Agents and Chemotherapy, Chicago, IL, Sep. 1991.

Isao Morishita et al., Drug Design and Delivery, vol. 7, 1991, pp. 309-319.

Farmacia Practica DeRemington, Second Spanish Ed., Uteha, Mexico, 1965, Chapters 36 and 38.

Remington's Pharm Sciences, 19Ed Spanish Farmacia Practica DeRemington, p. 2228 and 2229 (translation being obtained).

Yoshitomi, et al., Chem. Pharm. Bull, 40(7), 1902-1905, 1992.

Fiese, et al., Jrnl of Antimicrobial Chemotherapy, 1990, 25, suppl. A. pp. 39-47.

Anie, et al., Intrnl Jrnl of Pharmaceutics, 76, 1991, pp. 183-185.

Khosla, et al., Intrnl Jrnl of Pharmaceutics, 62, 1990, pp. R9-R11.

Knutson, et al., The Am Jrnl of Gastroenterology, 1989, vol. 84, No. 10, pp. 1278-1284.

Jobin, et al., Br. J. Clin. Pharmac, 1985, 19, pp. 97S-105S.

Blankenhom, Socl. Exp. Boil. Med, 1955, 88, pp. 356-362.

Graffner, et al., Pharm Research, vol. 7, No. 1, 1990, pp. 54-58.

Fischer, et al., Pharm Research, vol. 4, No. 6, 1987, pp. 480-485.

Welling, P., 1986, ACS Monograph 185, American Chemical Society, pp. 173-178.

Langenbucher, et al., Br. J. Clin. Pharmac, 1985, 19, pp. 151S-162S.

Handsfield Abstract from the 31st Interscience Conference on Antimicrobial Agents & Chemotherapy, 1991.

H. H. Handsfield et al., Sexually Transmitted Diseases, vol. 21(2), pp. 107-111, 1994.

Piero Periti, et al., Clinical Pharmacokinetics, vol. 16, pp. 193-214, 1989.

* cited by examiner

CONTROLLED-RELEASE DOSAGE FORMS OF AZITHROMYCIN

This application is a continuation of copending U.S. Ser. No. 09/577,059 (fully incorporated herein by reference), filed May 22, 2000, which is a division of U.S. Ser. No. 08/727,634 (fully incorporated herein by reference), filed Nov. 4, 1996, now U.S. Pat. No. 6,068,859, issued May 30, 2000, which is a 371 of PCT/IB95/00264, filed Apr. 13, 1995, which is a continuation-in-part of U.S. Ser. No. 08/239,094, filed May 6, 1994, now abandoned.

FIELD OF THE INVENTION

This invention relates to a controlled-release dosage form of azithromycin having an improved side effect profile, to a process for preparing the dosage form, and to a method of treating a microbial infection, comprising administering azithromycin in such a controlled-release dosage form to a mammal, including a human patient, in need of such treatment.

BACKGROUND OF THE INVENTION

Azithromycin is the U.S.A.N. (generic name) for 9a-aza-9a-methyl-9-deoxo-9a-homoerythromycin A, a broad spectrum antimicrobial compound derived from erythromycin A. Azithromycin was independently discovered by Bright, U.S. Pat. No. 4,474,768 and Kobrehel et al., U.S. Pat. No. 4,517,359. These patents disclose that azithromycin and certain derivatives thereof possess antimicrobial properties and are accordingly useful as antibiotics.

It is widely known that oral dosing of azithromycin can result in the occurrence, in some patients, of adverse gastrointestinal (GI) side effects, such as cramping, diarrhea, nausea, and vomiting. In combined clinical studies of azithromycin involving 3,995 patients (all dose levels combined), 9.6% of patients reported gastrointestinal side effects. The most frequent of these side effects were diarrhea (3.6%), nausea (2.6%), and abdominal pain 2.5%) (Hopkins, Am. J. Med. 91(suppl 3A) (1991) 40S–45S).

The incidence of gastrointestinal side effects is higher at higher doses than at lower doses. For example, a common 5 day course of azithromycin therapy consists of 500 mg on day 1 followed by 250 mg on days 2, 3, 4, and 5. For this course of therapy, the reported incidence of various, gastrointestinal side effects was 5% diarrhea/loose stools, 3% abdominal pain, and 3% nausea (Zithromax (Trademark of Pfizer Inc.) capsule package insert). After a single 1 g oral dose, the reported incidence of various gastrointestinal side effects was 7% diarrhea/loose stools, 5% nausea, and 2% vomiting (Zithromax capsule package insert).

It is also known that azithromycin can cause gastrointestinal side-effects in non-human mammals, e.g. dogs.

An improved dosage form of azithromycin which permitted oral dosing of high doses of azithromycin (e.g., 2 g) with relatively reduced side effects would permit wider application of single dose azithromycin therapy, and would accordingly provide a significant improvement in dosing compliance and convenience. Likewise, an improved dosage form which lowered the incidence of gastrointestinal side-effects at lower doses would also be of significant value.

SUMMARY OF THE INVENTION

This invention provides a controlled release dosage form of azithromycin which decreases, relative to currently marketed instant release azithromycin capsule dosage forms which deliver an equivalent dose, the incidence and/or severity of gastrointestinal side effects. The dosage form can operate by effecting the release of azithromycin at a rate sufficiently slow to ameliorate side effects. The dosage form can also operate by releasing the bulk of the azithromycin contained therein in the portion of the GI tract distal to the duodenum. Specific embodiments can be in the form of a sustained release oral dosage form or, alternatively, in the form of a delayed release oral dosage form, or, alternatively, in the form of an oral dosage form which exhibits a combination of sustained release and delayed release characteristics. The term "controlled" is generic to "sustained" and "delayed". Dosage forms which release more than 70% of their contained azithromycin within one half hour or less are not "controlled release", and form no part of this invention.

In a specific aspect this invention provides a sustained release dosage form comprising azithromycin and a pharmaceutically acceptable carrier which, following ingestion by a mammal in need of such treatment, releases azithromycin to said mammal's gastrointestinal tract at a rate such that the total amount of azithromycin released therein is:

not more than about 4 mg of azithromycin per kg of mammal weight in the first 15 minutes after ingestion, not more than about 10 mg of azithromycin per kg of mammal weight in the first hour after ingestion, not more than about 20 mg of azithromycin per kg of mammal weight in the first 2 hours after ingestion, not more than about 30 mg of azithromycin per kg of mammal weight in the first 4 hours after ingestion, and not more than about 40 mg of azithromycin per kg of mammal weight in the first 6 hours after ingestion.

The above criteria are herein referred to as the "weight criteria".

In a further specific aspect, the invention provides an oral delayed release dosage form of azithromycin, comprising azithromycin and a pharmaceutically acceptable carrier, which releases not more than about 10% of its incorporated azithromycin in the stomach, and which releases no more than an additional 10% during the first 15 minutes after the dosage form has entered the duodenum. Once having entered the duodenum and moved distally through and beyond this intestinal segment for at least 15 minutes, the rate at which the dosage form releases azithromycin is not critical, so long as substantially all of the azithromycin therein is released for absorption, as opposed to being excreted.

In a further specific aspect, this invention provides a sustained release dosage form, comprising azithromycin and a pharmaceutically acceptable carrier, which releases a total amount of azithromycin at the following rate following ingestion by a mammal: not more than about 200 mg azithromycin total in the first 15 minutes after ingestion, not more than about 500 mg of azithromycin total in the first hour after ingestion, not more than about 1000 mg total in the first two hours after ingestion, not more than about 1500 mg total in the first four hours after ingestion, and not more than about 2000 mg total in the first six hours after ingestion. The preceeding criteria are referred to herein as the "temporal criteria". Rates of azithromycin release lower than the rate just described are also within the scope of the invention and may produce even better side effect profiles, particularly for patients under 50 kg weight, e.g., children. Thus an azithromycin release rate of (each amount representing the total (i.e., cumulative) amount released), for example, less than 200 mg in the first 15 minutes after ingestion, less than 400 mg in the first hour after ingestion, less than 750 mg in the first two hours after ingestion, less than 1250 mg in the first 4 hours after ingestion, and less than 1500 mg in the first 6 hours after ingestion represents a release profile within the scope of the invention and may be even more efficacious for ameliorating side effects. Once six hours following ingestion has passed, the rate at which the dosage form releases azithromycin (for example, if the dosage form contained more than 2 g of azithromycin to begin with) is not critical. The rate must, of course, be high enough to provide therapeutic efficacy, that is, a therapeutically sufficient amount of azithromycin should be delivered from the dosage form before the dosage form is excreted with the feces.

For example, FIG. 1 displays hypothetical release profiles 3 and 4 for a dosage form which is within the scope of the invention. The thick bolded stair-step profile 1 in fact defines the release profile of the temporal criteria. Profile 2 represents a hypothetical release profile outside the scope of the invention.

It is noted that, although the temporal and weight criteria define a release profile extending for as long as 6 hours, a dosage form according to the invention can release substantially all of its azithromycin well before 6 hours, so long as it otherwise fits within the defined rates. Dosage forms according to the invention which contain relatively low amounts of azithromycin (e.g., less than 1000 mg) may well release substantially all their azithromycin within a few hours.

The term "ingestion" as used herein is essentially synonymous with "swallowing".

The invention is particularly useful for administering relatively large amounts of azithromycin to a patient. The amount of azithromycin contained within the dosage form is preferably at least 1 gram, and can be as high as 7 grams or more. The amount contained in the dosage form is preferably 1.5 to 4 grams, most preferably 1.5 to 3 grams. The dosage form can be unitary as in the case of a bolus, or divided e.g., constituted by two or more units (such as capsules or tablets) which are taken at or about the same time.

Azithromycin can be employed in the dosage forms of this invention in the form of its pharmaceutically acceptable salts, and also in anhydrous as well as hydrated forms. All such forms are within the scope of this invention. The azithromycin employed is preferably the dihydrate, disclosed for example in published European Patent Application 0 298 650 A2. Reference to "azithromycin" in terms of therapeutic amounts or in release rates in the claims is to active azithromycin, i.e., the non-salt, non-hydrated macrolide molecule having a molecular weight of 749.

The dosage forms which constitute the subject matter of the invention are, as mentioned, controlled release formulations.

In the case of sustained release embodiments, the dosage form can be in the form of a tablet, a capsule, a multiparticulate form, or a unit dose packet (sometimes referred to in the art as a "sachet").

The term "tablet" is intended to embrace compressed tablets, coated tablets, matrix tablets, osmotic tablets, and other forms known in the art, as more fully disclosed below.

The term "capsule" is intended to embrace capsules in which the body of the capsule disintegrates after ingestion to release particulate contents which exhibit the desired sustained-release behavior, and also capsules for which the body of the capsule remains substantially intact during its residence in the GI tract.

The term "multiparticulate" is intended to embrace a dosage form comprising a multiplicity of particles whose totality represents the intended therapeutically useful dose of azithromycin. The particles generally are of a diameter from about 50 microns to about 0.3 cm, with a preferred range of 100 µM to 1 mm. The use of these and other terms is more fully set out below. Multiparticulates represent a preferred embodiment for sustained-release because they are amenable to use in scaling dosage forms according to the weight of an individual animal (e.g., a horse), according to the weight criteria previously set forth, by simply scaling the number of particles in the dosage form to conform with the animal's weight.

In a further aspect, this invention provides a process for preparing sustained-release dosage forms of azithromycin, comprising the steps of granulating azithromycin bulk drug substance with a binder, essentially immediately thereafter coating the granulation with a polymer coating of controlled permeability to azithromycin, and thereafter further coating said granulation with additional polymer of controlled permeability to azithromycin until enough of the polymer has been applied to effect the desired sustained release rate or profile.

In a further aspect, this invention provides a method for treating a microbial infection, comprising administering to a mammal in need of such treatment, including a human patient, a therapeutically effective amount of azithromycin in a controlled-release oral dosage form which releases the azithromycin according to the release rate described above.

In the case of delayed release embodiments, the dosage form can be in the form of a tablet, capsule, multiparticulate, suspension, or sachet, provided that the dosage form delivers the majority of its azithromycin to regions of the gastrointestinal tract distal to the duodenum. A variety of dosage form embodiments and/or structures may be used to achieve this goal, as hereinafter further described in detail. Multiparticulate, bead, or other particle dosage forms may be multiply loaded into a gelatin capsule, or may be compressed into a tablet.

It is an object of this invention to decrease the incidence and severity of azithromycin-induced GI side effects. This is particularly important at high doses, for example 2 g and up, at which the incidence of gastrointestinal side effects can be relatively high. This object is effected by minimizing exposure of the duodenum to azithromycin in at least a portion of azithromycin-dosed patients, thereby reducing the overall incidence and severity of azithromycin-induced gastrointestinal side effects.

The inventors conducted a series of studies in man in which the incidence and severity of gastrointestinal side effects were assessed after dosing azithromycin intravenously, orally, duodenally (via nasoenteric intubation), and ileally (via nasoenteric intubation). The studies demonstrated that the incidence of gastrointestinal side effects is relatively low after intravenous dosing, even at doses which are equivalent to a 5.4 g oral dose. Thus, while not wishing to be limited by or to any particular theory or mechanism, the gastrointestinal side effects of orally dosed azithromycin appear to be mediated by local interactions between azithromycin and the intestinal wall. Furthermore, the nasoenteric intubation studies demonstrated that duodenal azithromycin dosing results in more severe gastrointestinal side effects than does ileal dosing. The inventors accordingly determined that dosing azithromycin in a manner which reduces exposure of the duodenum to high concentrations of the drug results in decreased gastrointestinal side effects.

Dosing azithromycin orally in conventional non-controlled-release capsules results in relatively extensive exposure of drug to the duodenum. Dosing of azithromycin in conventional enteric dosage forms which prevent significant dissolution of the drug in the stomach can also expose the duodenum to a large proportion of the azithromycin dose. It is accordingly a further object of this invention to provide dosage forms which deliver therapeutically useful doses of azithromycin, while reducing localized exposure of azithromycin throughout the GI tract, especially at the duodenum, thereby providing decreased gastrointestinal side effects.

It is noted that controlled-release dosage forms of various types are known and employed conventionally in the art to provide reduced dosing frequency for short half-life compounds and to reduce fluctuations in plasma concentrations, sometimes imparting an improved safety/efficacy profile. Because elimination of azithromycin from the human body is characterized by a long half-life of about 69 hours, however, it is surprising that a controlled-release (either sustained or delayed) dosage form would offer any benefit.

DETAILED DISCUSSION

Figure 1:
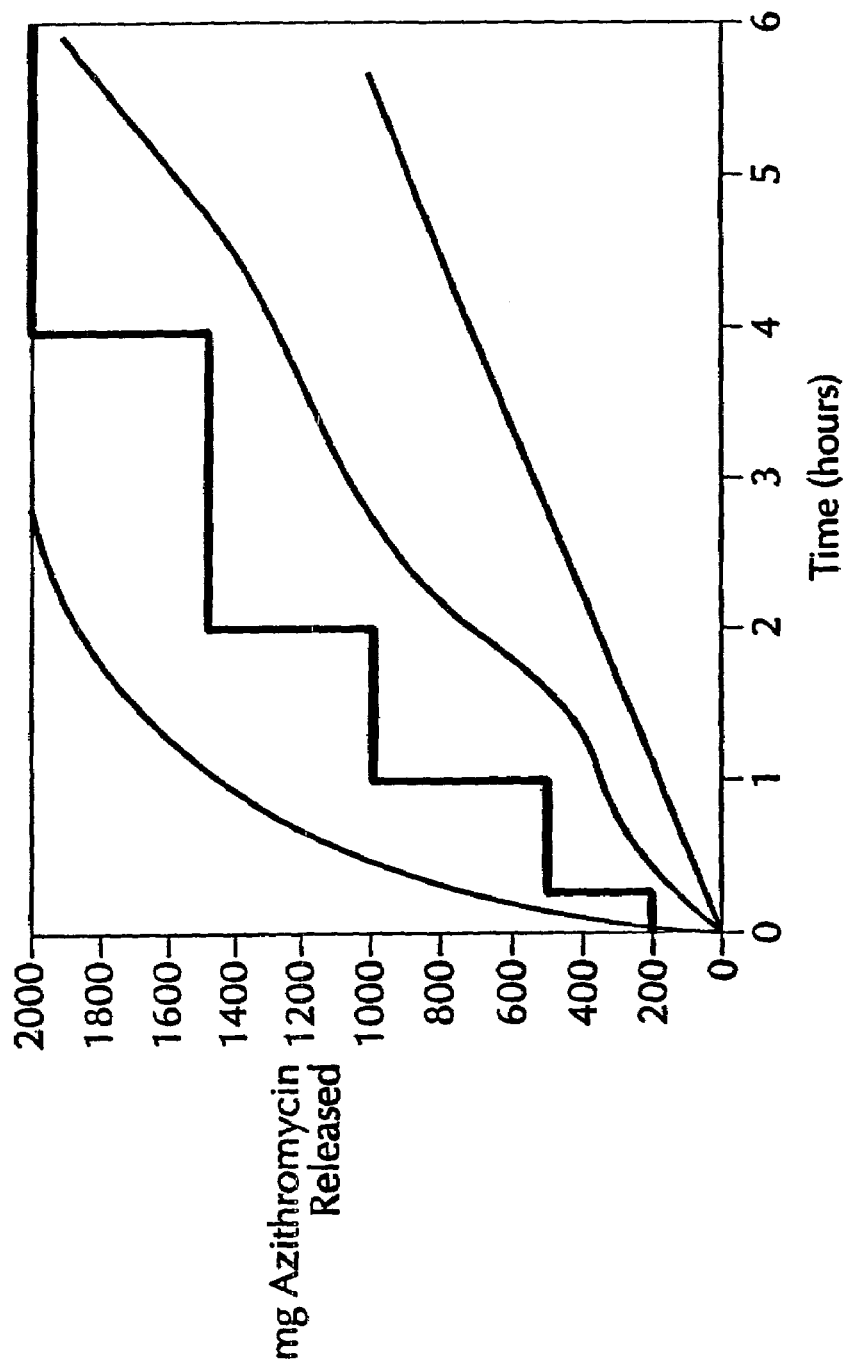
FIG. 1 is a graphical illustration of a release profile as broadly defined by the temporal criteria (profile 1), of several hypothetical azithromycin release profiles within the scope of the invention (profiles 3 and 4), and of a hypothetical release profile outside the scope of the invention (profile 2).

For the purpose of this application, various embodiments of "controlled release dosage forms of azithromycin" have been described as "sustained release" embodiments or "delayed release" embodiments, for ease of description. Without intending to be limiting, sustained release dosage forms of azithromycin are those which slowly release azithromycin. Delayed release dosage forms of azithromycin are those which release little or no azithromycin for a predetermined time, then release azithromycin quickly or in a sustained fashion. It will be appreciated by those skilled in the art that certain "sustained release" embodiments will also fall under the general rubric of "delayed release" embodiments, and vice versa. For example, sustained release osmotic pump devices generally exhibit a "lag time" after ingestion, during which time the osmotic pressure in the device is increasing and during which time little or no drug is released. Thus, an azithromycin osmotic pump device may be considered both a sustained release and a delayed release device. Embodiments of the current invention include all controlled release dosage forms of azithromycin which meet one or both of the in vitro tests described herein (see "Examples" section) for a "sustained release dosage form", or a "delayed release dosage form".

Sustained Release

The sustained-release dosage forms of this invention can be widely implemented. For purposes of discussion, not limitation, the many embodiments hereunder can be grouped into classes according to design and principle of operation.

A first class includes matrix systems, in which azithromycin is embedded or dispersed in a matrix of another material that serves to retard the release of azithromycin into an aqueous environment (i.e., the lumenal fluid of the GI tract). When azithromycin is dispersed in a matrix of this sort, release of the drug takes place principally from the surface of the matrix. Thus the drug is released from the surface of a device which incorporates the matrix after it diffuses through the matrix or when the surface of the device erodes, exposing the drug. In some embodiments, both mechanisms can operate simultaneously. The matrix systems may be large, i.e., tablet sized (about 1 cm), or small (<0.3 cm). The system may be unitary (e.g, a bolus), may be divided (as previously discussed) by virtue of being composed of several sub-units (for example, several capsules which constitute a single dose) which are administerd substantially simultaneously, or may comprise a plurality of particles, referred to herein as a multiparticulate. A multiparticulate can have numerous formulation applications. For example, a multiparticulate may be used as a powder for filling a capsule shell, or used per se for mixing with food (e.g, ice cream) to increase palatability.

The size of the matrix system can affect the rate of azithromycin release, therefore, a large matrix system such as a tablet will, in general, have a different composition from a small one such as a multiparticulate. The effect of the size of the matrix system on the kinetics of azithromycin release follows scaling behavior well known in the study of diffusion. By way of illustration, the following table shows the diffusion coefficient of azithromycin required to achieve a characteristic time for release of 10 hours for matrix systems of different sizes.

| radius (cm) | diffusion coefficient (cm$^2$/s) |
| --- | --- |
| 0.0025 (50 μm diameter) | $1.7 \times 10^{-10}$ |
| 0.1 (2 mm diameter) | $3 \times 10^{-7}$ |
| 0.5 (1 cm diameter) | $7 \times 10^{-6}$ |

The above table illustrates that diffusion coefficients change by orders of magnitude as the desired size of the device changes. The high and low values represent approximate upper and lower limits for matrix devices of this invention. That is, materials which exhibit a diffusion coefficient lower than about $10^{-10}$ are likely unsuitable for this invention as they are approaching, relatively speaking, being totally impermeable to azithromycin. Materials characterized by a diffusion coefficient higher than about $7 \times 10^{-6}$ are likely also unsuitable as they are approaching, relatively speaking, being an instant or fast-release device. Materials at the low end of the diffusion coefficient scale are polymers such as cellulose acetate. Conversely, materials at the upper end of the scale are materials such as hydrogels. The rate of diffusion for any particular device can accordingly be tailored by the material or materials selected.

In the same manner but different words, in general, sustained release devices of this invention should be implemented to release the azithromycin contained therein over a period of up to 6 h, and possibly longer. The device can accordingly be engineered according to the equation $RT = r^2/D$ wherein RT stands for the total release time of a contained dosage, r represents the radius of the device, and D stands for the diffusion coefficient of azithromycin in the matrix material. The equation again illustrates that suitable dosage forms can be engineered as a trade-off between the size of the device and the diffusion coefficient of the matrix material. If a spherical dosage form is not employed, then r will, of course, be replaced by other suitable dimension as known in the art, such as the half thickness of a cube, short axis for an ellipsoid, and the like.

For purposes of further illustration, to obtain a sustained-release matrix in a particle of about 50 µm in diameter, a matrix material of a polymer such as cellulose acetate or a similar material will likely be required, the slow diffusing matrix material tending to offset the tendency of the small particle size to diffuse quickly. By contrast, in order to obtain sustained-release in a large (e.g., 1 cm) device, a material which is mostly liquid-lik (e.g., a hydrogel, see below) will likely be required. For devices of an intermediate size, e.g., about 1 mm in diameter, a matrix material of intermediate characteristics can be employed.

It is also noted that the effective diffusion coefficient of azithromycin in a dense material may be increased to the the desired value by the addition of plasticizers, pores, or pore-inducing additives, as known in the art. Slowly-hydrating materials may also be used to give the desired intermediate diffusion rates. The multiplicity of variables affecting release of azithromycin from matrix devices permits abundant flexibility in the design of devices of different materials, sizes, and release times. Examples of modifications of azithromycin release profiles from the specific embodiments of the examples within the scope of this invention are disclosed in detail below.

A preferred embodiment, a matrix multiparticulate, comprises a plurality of azithromycin-containing particles, each particle comprising a mixture of azithromycin with one or more excipients selected to form a matrix capable of limiting the dissolution rate of the azithromycin into an aqueous medium. The matrix materials useful for this embodiment are generally water-insoluble materials such as waxes, cellulose, or other water-insoluble polymers. If needed, the matrix materials may optionally be formulated with water-soluble materials which can be used as binders or as permeability-modifying agents. Matrix materials useful for the manufacture of these dosage forms include microcrystalline cellulose such as Avicel (registered trademark of FMC Corp., Philadelphia, Pa.), including grades of microcrystalline cellulose to which binders such as hydroxypropyl methyl cellulose have been added, waxes such as paraffin, modified vegetable oils, carnauba wax, hydrogenated castor oil, beeswax, and the like, as well as synthetic polymers such as poly(vinyl chloride), poly(vinyl acetate), copolymers of vinyl acetate and ethylene, polystyrene, and the like. Water soluble binders or release modifying agents which can optionally be formulated into the matrix include water-soluble polymers such as hydroxypropyl cellulose (HPC), hydroxypropyl methyl cellulose (HPMC), methyl cellulose, poly (N-vinyl-2-pyrrolidinone) (PVP), poly(ethylene oxide) (PEO), poly(vinyl alcohol) (PVA), xanthan gum, carrageenan, and other such natural and synthetic materials. In addition, materials which function as release-modifying agents include water-soluble materials such as sugars or salts. Preferred water-soluble materials include lactose, sucrose, glucose, and mannitol, as well as HPC, HPMC, and PVP.

A preferred process for manufacturing matrix multiparticulates is the extrusion/spheronization process. For this process, the azithromycin is wet-massed with a binder, extruded through a perforated plate or die, and placed on a rotating disk. The extrudate ideally breaks into pieces which are rounded into spheres, spheroids, or rounded rods on the rotating plate. A preferred process and composition for this method involves using water to wet-mass a blend comprising about 20 to 75% of micro-crystalline cellulose blended with, correspondingly, about 80 to 25% azithromycin.

A further preferred process for manufacturing matrix multiparticulates is the preparation of wax granules. In this process, a desired amount of azithromycin is stirred with liquid wax to form a homogeneous mixture, cooled and then forced through a screen to form granules. Preferred matrix materials are waxy substances. Especially preferred are hydrogenated castor oil and carnauba wax and stearyl alcohol.

A further preferred process for manufacturing matrix multiparticulates involves using an organic solvent to aid mixing of the azithromycin with the matrix material. This technique can be used when it is desired to utilize a matrix material with an unsuitably high melting point that, if the material were employed in a molten state, would cause decomposition of the drug or of the matrix material, or would result in an unacceptable melt viscosity, thereby preventing mixing of azithromycin with the matrix material. Azithromycin and matrix material may be combined with a modest amount of solvent to form a paste, and then forced through a screen to form granules from which the solvent is then removed. Alternatively, azithromycin and matrix material may be combined with enough solvent to completely dissolve the matrix material and the resulting solution (which may contain solid drug particles) spray dried to form the particulate dosage form. This technique is preferred when the matrix material is a high molecular weight synthetic polymer such as a cellulose ether or cellulose ester. Solvents typically employed for the process include acetone, ethanol, isopropanol, ethyl acetate, and mixtures of two or more.

Once formed, azithromycin matrix multiparticulates may be blended with compressible excipients such as lactose, microcrystalline cellulose, dicalcium phosphate, and the like and the blend compressed to form a tablet. Disintegrants such as sodium starch glycolate or crosslinked poly(vinyl pyrrolidone) are also usefully employed. Tablets prepared by this method disintegrate when placed in an aqueous medium (such as the GI tract), thereby exposing the multiparticulate matrix which releases azithromycin therefrom.

A further embodiment of a matrix system has the form of a hydrophilic matrix tablet containing azithromycin and an amount of hydrophilic polymer sufficient to provide a useful degree of control over the azithromycin dissolution. Hydrophilic polymers useful for forming the matrix include hydroxyprepylmethyl cellulose (HPMC), hydroxypropyl cellulose (HPC), poly (ethylene oxide), poly(vinyl alcohol), xanthan gum, carbomer, carrageenan, and zooglan. A preferred material is HPMC. Other similar hydrophilic polymers may also be employed. In use, the hydrophilic material is swollen by, and eventually dissolves in, water. The azithromycin is released both by diffusion from the matrix and by erosion of the matrix. The azithromycin dissolution rate of these hydrophilic matrix tablets may be controlled by the amount and molecular weight of hydrophilic polymer employed. In general, using a greater amount of the hydrophilic polymer decreases the dissolution rate, as does using a higher molecular weight polymer. Using a lower molecular weight polymer increases the dissolution rate. The dissolution rate may also be controlled by the use of water-soluble additives such as sugars, salts, or soluble polymers. Examples of these additives are sugars such as lactose, sucrose, or mannitol, salts such as NaCl, KCl, $NaHCO_3$, and water soluble polymers such as PNVP or PVP, low molecular weight HPC or HMPC or methyl cellulose. In general, increasing the fraction of soluble material in the formulation increases the release rate. A matrix tablet typically comprises about 20 to 90% by weight of azithromycin and about 80 to 10% by weight of polymer.

A preferred matrix tablet comprises, by weight, about 50% to about 80% azithromycin, about 15% to about 35% HPMC, 0% to about 35% lactose, 0% to about 15% PVP, 0% to about 20% microcrystalline cellulose, and about 0.25% to about 2% magnesium stearate.

The matrix systems as a class often exhibit non-constant release of the drug from the matrix. This result may be a consequence of the diffusive mechanism of drug release, and modifications to the geometry of the dosage form can be used to advantage to make the release rate of the drug more constant as detailed below.

In a further embodiment, an azithromycin matrix tablet is coated with an impermeable coating, and an orifice (for example, a circular hole or a rectangular opening) is provided by which the content of the tablet is exposed to the aqueous GI tract. These embodiments are along the lines of those presented in in U.S. Pat. No. 4,792,448 to Ranade, herein incorporated by reference. The opening is typically of a size such that the area of the exposed underlying azithromycin composition constitutes less than about 40% of the surface area of the device, preferably less than about 15%.

In a preferred embodiment, an azithromycin matrix tablet is coated with an impermeable material on part of its surface, e.g. on one or both tablet faces, or on the tablet radial surface.

In a preferred embodiment, an azithromycin matrix tablet is coated with an impermeable material and an opening for drug transport produced by drilling a hole through the coating. The hole may be through the coating only, or may extend as a passageway into the tablet.

In a further preferred embodiment, an azithromycin matrix tablet is coated with an impermeable material and a passageway for drug transport produced by drilling a passageway through the entire tablet.

In a further preferred embodiment, an azithromycin matrix tablet is coated with an impermeable material and one or more passageways for drug transport are produced by removing one or more strips from the impermeable coating or by cutting one or more slits through the coating, preferably on the radial surface or land of the tablet.

In a preferred embodiment, an azithromycin matrix tablet is shaped in the form of a cone and completely coated with an impermeable material. A passageway for drug transport is produced by cutting off the tip of the cone.

In a further preferred embodiment, an azithromycin matrix tablet is shaped in the form of a hemisphere and completely coated with an impermeable material. A passageway for drug transport is produced by drilling a hole in the center of the flat face of the hemisphere.

In a further preferred embodiment, an azithromycin matrix tablet is shaped in the form of a half-cylinder and completely coated with an impermeable material. A passageway for drug transport is produced by cutting a slit through (or removing a strip from) the impermeable coating along the axis of the half-cylinder along the centerline of the flat face of the half-cylinder.

Those skilled in the art will appreciate that the geometric modifications to the embodiments described above can be equivalently produced by more than one method. For example, cutting or drilling to make a passageway for drug transport can be achieved by other operations such as by a technique which produces the desired partial coating directly.

By "impermeable material" is meant a material having sufficient thickness and impermeability to azithromycin such that no significant transport of azithromycin can take place through the material during the time scale of the intended drug release (i.e., several hours to about a day). Such a coating can be obtained by selecting a coating material with a sufficiently low diffusion coefficient for azithromycin and applying it sufficiently thickly. Materials for forming the impermeable coating of these embodiments include substantially all materials in which the diffusion coefficient of azithromycin is less than about $10^{-7}$ cm$^2$/s. It is noted that the preceding diffusion coefficient can be amply sufficient for a matrix device, as discussed above. In a device of the type now under discussion which has been provided with a macroscopic opening, however, a material with this diffusion coefficient (and almost any membrane material that is not a liquid) looks to the contained azithromycin, by contrast, as though it is impermeable because the majority of transport is through the opening. Preferred coating materials include film-forming polymers and waxes. Especially preferred are thermoplastic polymers, such as poly(ethylene-co-vinyl acetate), poly(vinyl chloride), ethylcellulose, and cellulose acetate. These materials exhibit the desired low permeation rate of azithromycin when applied as coatings of thickness greater than about 100 μm.

A further sustained release matrix system comprises azithromycin dispersed in a hydrogel matrix. This embodiment differs from the hydrophilic matrix tablet discussed above in that the hydrogel of this embodiment is not a compressed tablet of erodible granular material, but rather a monolithic polymer network. As known in the art, a hydrogel is a water-swellable network polymer. Hydrogels are preferred materials for matrix devices because they can absorb or be made to contain a large volume fraction of water, thereby permitting diffusion of solvated drug within the matrix. Diffusion coefficients of drugs in hydrogels are characteristically high, and for highly water-swollen gels, the diffusion coefficient of the drug in the gel may approach the value in pure water. This high diffusion coefficient permits practical release rates from relatively large devices (i.e., it is not necessary to form microparticles). Although hydrogel devices can be prepared, loaded with azithromycin, stored, dispensed and dosed in the fully hydrated state, it is preferred that they be stored, dispensed, and dosed in a dry state. In addition to stability and convenience, dry state dosing of hydrogel devices provides good azithromycin release kinetics. Preferred materials for forming hydrogels include hydrophilic vinyl and acrylic polymers, polysaccharides such as calcium alginate, and poly(ethylene oxide). Especially preferred are poly(2-hydroxyethyl-methacrylate), poly(acrylic acid), poly(methacrylic acid), poly(N-vinyl-2-pyrolidinone), poly(vinyl alcohol) and their copolymers with each other and with hydrophobic monomers such as methyl methacrylate, vinyl acetate, and the like. Also preferred are hydrophilic polyurethanes containing large poly(ethylene oxide) blocks. Other preferred materials include hydrogels comprising interpenetrating networks of polymers, which may be formed by addition or by condensation polymerization, the components of which may comprise hydrophilic and hydrophobic monomers such as those just enumerated.

A second class of azithromycin sustained-release dosage forms of this invention includes membrane-moderated or reservoir systems. In this class, a reservoir of azithromycin is surrounded by a rate-limiting membrane. The azithromycin traverses the membrane by mass transport mechanisms well known in the art, including but not limited to dissolution in the membrane followed by diffusion across the membrane or diffusion through liquid-filled pores within the membrane. These individual reservoir system dosage forms may be large, as in the case of a tablet containing a single large reservoir, or multiparticulate, as in the case of a capsule containing a plurality of reservoir particles, each individually coated with a membrane. The coating can be non-porous, yet permeable to azithromycin (for example azithromycin may diffuse directly through the membrane), or it may be porous. As with other embodiments of this invention, the particular mechanism of transport is not believed to be critical.

Sustained release coatings as known in the art may be employed to fabricate the membrane, especially polymer coatings, such as a cellulose ester or ether, an acrylic polymer, or a mixture of polymers. Preferred materials include ethyl cellulose, cellulose acetate and cellulose acetate butyrate. The polymer may be applied as a solution in an organic solvent or as an aqueous dispersion or latex. The coating operation may be conducted in standard equipment such as a fluid bed coater, a Wurster coater, or a rotary bed coater.

If desired, the permeability of the coating may be adjusted by blending of two or more materials. A particularly useful process for tailoring the porosity of the coating comprises adding a pre-determined amount of a finely-divided water-soluble material, such as sugars or salts or water-soluble polymers to a solution or dispersion (e.g., an aqueous latex) of the membrane-forming polymer to be used. When the dosage form is ingested into the aqueous medium of the GI tract, these water soluble membrane additives are leached out of the membrane, leaving pores which facilitate release of the drug. The membrane coating can also be modified by the addition of plasticizers, as known in the art.

A particularly useful variation of the process for applying a membrane coating comprises dissolving the coating polymer in a mixture of solvents chosen such that as the coating dries, a phase inversion takes place in the applied coating solution, resulting in a membrane with a porous structure. Numerous examples of this type of coating system are given in European Patent Specification 0 357 369 B1, published Mar. 7, 1990, herein incorporated by reference. In general, a support for mechanically strengthening the membrane is not required.

The morphology of the membrane is not of critical importance so long as the permeability characteristics enumerated herein are met. The membrane can be amorphous or crystalline. It can have any category of morphology produced by any particular process and can be, for example, an interfacially-polymerized membrane (which comprises a thin rate-limiting skin on a porous support), a porous hydrophilic membrane, a porous hydrophobic membrane, a hydrogel membrane, an ionic membrane, and other such materials which are characterized by controlled permeability to azithromycin.

A useful reservoir system embodiment is a capsule having a shell comprising the material of the rate-limiting membrane, including any of the membrane materials previously discussed, and filled with an azithromycin drug composition. A particular advantage of this configuration is that the capsule may be prepared independently of the drug composition, thus process conditions that would adversely affect the drug can be used to prepare the capsule. A preferred embodiment is a capsule having a shell made of a porous or a permeable polymer made by a thermal forming process. An especially preferred embodiment is a capsule shell in the form of an asymmetric membrane; i.e., a membrane that has a thin skin on one surface and most of whose thickness is constituted of a highly permeable porous material. A preferred process for preparation of asymmetric membrane capsules comprises a solvent exchange phase inversion, wherein a solution of polymer, coated on a capsule-shaped mold, is induced to phase-separate by exchanging the solvent with a miscible non-solvent. Examples of asymmetric membranes useful in this invention are disclosed in the aforementioned European Patent Specification 0 357 369 B1.

A preferred embodiment of the class of reservoir systems comprises a multiparticulate wherein each particle is coated with a polymer designed to, yield sustained release of azithromycin. The multiparticulate particles each, comprise azithromycin and one or more excipients as needed for fabrication and performance. The size of individual particles, as previously mentioned, is generally between about 50 μm and about 3 mm, although beads of a size outside this range may also be useful. In general, the beads comprise azithromycin and one or more binders. As it is generally desirable to produce dosage forms which are small and easy to swallow, beads which contain a high fraction of azithromycin relative to excipients are preferred. Binders useful in fabrication of these beads include microcrystalline cellulose (e.g., Avicel®, FMC Corp.), hydroxypropyl cellulose (HPC), hydroxypropyl methyl cellulose (HPMC), and related materials or combinations thereof. In general, binders which are useful in granulation and tabletting, such as starch, pregelatinized starch, and poly (N-vinyl-2-pyrrolidinone) (PVP) may also be used to form multiparticulates.

Reservoir system azithromycin multiparticulates may be prepared using techniques known to those skilled in the art, including, but not limited to, the techniques of extrusion and spheronization, wet granulation, fluid bed granulation, and rotary bed granulation. In addition, the beads may also be prepared by building the azithromycin composition (drug plus excipients) up on a seed core (such as a non-pareil seed) by a drug-layering technique such as powder coating or by applying the azithromycin composition by spraying a solution or dispersion of azithromycin in an appropriate binder solution onto seed cores in a fluidized bed such as a Wurster coater or a rotary processor. An example of a suitable composition and method is to spray a dispersion of an azithromycin/hydroxypropylcellulose composition in water. Advantageously, azithromycin can be loaded in the aqueous composition beyond its solubility limit in water.

A preferred method for manufacturing the multiparticulate cores of this embodiment is the extrusion/spheronization process, as previously discussed for matrix multiparticulates. A preferred process and composition for this method involves using water to wet-mass a blend of about 5 to 75% of micro-crystalline cellulose with correspondingly about 95 to 25% azithromycin. Especially preferred is the use of about 5–30% microcrystalline cellulose with correspondingly about 95–70% azithromycin.

A sustained release coating as known in the art, especially polymer coatings, may be employed to fabricate the membrane, as previously, discussed for reservoir systems. Suitable and preferred polymer coating materials, equipment, and coating methods also include those previously discussed.

The rate of azithromycin release from the coated multiparticulates can also be controlled by factors such as the composition and binder content of the drug containing core, the thickness and permeability of the coating, and the surface-to-volume ratio of the multiparticulates. It will be appreciated by those skilled in the art that increasing the thickness of the coating will decrease the release rate, whereas increasing the permeability of the coating or the surface-to-volume ratio of the multiparticulates will increase the release rate. If desired, the permeability of the coating may be adjusted by blending of two or more materials. A useful series of coatings comprises mixtures of water-insoluble and water-soluble polymers, for example, ethylcellulose and hydroxypropyl methylcellulose, respectively. A particularly useful modification to the coating is the addition of finely-divided water-soluble material, such as sugars or salts. When placed in aqueous medium, these water soluble membrane additives are leached out of the membrane, leaving pores which facilitate delivery of the drug. The membrane coating may also be modified by the addition of plasticizers, as is known to those skilled in the art. A particularly useful variation of the membrane coating utilizes a mixture of solvents chosen such that as the coating dries, a phase inversion takes place in the applied coating solution, resulting in a membrane with a porous structure.

A preferred embodiment is a multiparticulate comprising about 95% azithromycin, the individual particles being coated with an aqueous dispersion of ethyl cellulose, which dries to form a continuous film.

A further preferred embodiment is obtained when the azithromycin beads are less than about 400 μm in size and are coated with a phase inversion membrane of ethyl cellulose or cellulose acetate.

An especially preferred embodiment is obtained when the azithromycin beads are less than about 400 μm in size and are coated with an aqueous dispersion of ethyl cellulose, which dries to form a continuous film.

An even more especially preferred embodiment is obtained when the azithromycin beads are less than about 300 μm in size and are coated with an aqueous dispersion of ethyl cellulose, which dries to form a continuous film.

A third class of azithromycin sustained-release dosage forms includes the osmotic delivery devices or "osmotic pumps" as they are known in the art. Osmotic pumps comprise a core containing an osmotically effective composition surrounded by a semipermeable membrane. The term "semipermeable" in this context means that water can pass through the membrane, but solutes dissolved in water cannot. In use, when placed in an aqueous environment, the device imbibes water due to the osmotic activity of the core composition. Owing to the semipermeable nature of the surrounding membrane, the contents of the device (including the drug and any excipients) cannot pass through the non-porous regions of the membrane and are driven by osmotic pressure to leave the device through an opening or passageway pre-manufactured into the dosage form or, alternatively, formed in situ in the GI tract as by the bursting of intentionally-incorporated weak points in the coating under the influence of osmotic pressure. The osmotically effective composition includes water-soluble species, which generate a colloidal osmotic pressure, and water-swellable polymers. The drug itself (if highly water-soluble) may be an osmotically effective component of the mixture. Azithromycin fumarate has a solubility at pH 7 of about 100 mg/ml, corresponding to an osmotic pressure of about 3 atmospheres, enough to contribute some osmotic driving force. However, the solubility of azithromycin dihydrate in a self-buffered solution (pH>8) is much lower. Therefore, the osmotic effectiveness of azithromycin depends on the presence of acidic buffers in the formulation. The drug composition may be separated from the osmotically effective components by a movable partition or piston.

Materials useful for forming the semipermeable membrane include polyamides, polyesters, and cellulose derivatives. Preferred are cellulose ethers and esters. Especially preferred are cellulose acetate, cellulose acetate butyrate, and ethyl cellulose. Especially useful materials include those which spontaneously form one or more exit passageways, either during manufacturing or when placed in an environment of use. These preferred materials comprise porous polymers, the pores of which are formed by phase inversion during manufacturing, as described above, or by dissolution of a water-soluble component present in the membrane.

A class of materials which have particular utility for forming semipermeable membranes for use in osmotic delivery devices is that of porous hydrophobic polymers, as disclosed by commonly assigned co-pending U.S. application Ser. No. 08/096,144 filed Jul. 22, 1993, herein incorporated by reference. These materials are highly permeable to water, but highly impermeable to solutes dissolved in water. These materials owe their high water permeability to the presence of numerous microscopic pores (i.e., pores which are much larger than molecular dimensions). Despite their porosity, these materials are impermeable to molecules in aqueous solution because liquid water does not wet the pores. Water in the vapor phase is easily able to pass across membranes made from these materials.

A preferred embodiment of this class of osmotic delivery devices consists of a coated bi-layer tablet. The coating of such a tablet comprises a membrane permeable to water but substantially impermeable to azithromycin and excipients contained within. The coating contains one or more exit passageways in communication with the azithromycin-containing layer for delivering the drug composition. The tablet core consists of two layers: one layer containing the azithromycin composition and another layer consisting of an expandable hydrogel, with or without additional osmotic agents.

When placed in an aqueous medium, the tablet imbibes water through the membrane, causing the azithromycin composition to form a dispensible aqueous composition, and causing the hydrogel layer to expand and push against the azithromycin composition, forcing the azithromycin composition out of the exit passageway.

The rate of azithromycin delivery is controlled by such factors as the permeability and thickness of the coating, the water activity of the hydrogel layer, and the surface area of the device. Those skilled in the art will appreciate that increasing the thickness of the coating will reduce the release rate, whereas increasing the permeability of the coating or the water activity of the hydrogel layer or the surface area of the device will increase the release rate.

Exemplary materials which are useful to form the azithromycin composition, in addition to the azithromycin itself, include hydroxypropyl methyl cellulose, poly (ethylene oxide), poly (N-vinyl-2-pyrrolidinone) or PVP, and other pharmaceutically-acceptable carriers. In addition, osmagents such as sugars or salts, especially sucrose, mannitol, or sodium chloride, may be added. Materials which are useful for forming the hydrogel layer include sodium carboxymethyl cellulose, poly (ethylene oxide), poly (acrylic acid), sodium (poly-acrylate) and other high molecular-weight hydrophilic materials. Particularly useful are poly (ethylene oxide) having a molecular weight from about 4,000,000 to about 7,500,000 and sodium carboxymethyl cellulose having a molecular weight of about 200,000 to about 1,000,000.

Materials which are useful for forming the coating are cellulose esters, cellulose ethers, and cellulose ester-ethers. Preferred are cellulose acetate and ethylcellulose.

The exit passageway must be located on the side of the tablet containing the azithromycin composition. There may be more than one such exit passageway. The exit passageway may be produced by mechanical or by laser drilling, or by creating a difficult-to-coat region on the tablet by use of special tooling during tablet compression. The rate of azithromycin delivery from the device may be optimized so as to provide a method of delivering azithromycin to a mammal for optimum therapeutic effect.

A fourth class of azithromycin sustained release dosage forms of this invention comprises coated hydrogel tablets and multiparticulates, as described in co-pending commonly assigned U.S. Ser. No. 07/296,464, filed Jan. 12, 1989 (published as EP 378404 B1 Aug. 31, 1994), herein incorporated by reference. Coated hydrogel tablets comprise a tablet core comprising azithromycin and a swelling material, preferably a hydrogel polymer, coated with a membrane which contains holes or pores through which, in the aqueous use environment, the hydrogel can extrude and carry out the azithromycin. Alternatively, the membrane may contain polymeric or low molecular weight water soluble porosigens which dissolve in the aqueous use environment, providing pores through which the hydrogel and azithromycin may extrude. Examples of porosigens are water-soluble polymers such as hydroxypropylmethylcellulose, and low molecular weight compounds like glycerol, sucrose, glucose, and sodium chloride. In this fourth class of azithromycin sustained release dosage forms, the membrane material may comprise any film-forming polymer, including polymers which are water permeable or impermeable, providing that the membrane deposited on the tablet core is porous or contains water-soluble porosigens. Multiparticulates (or beads) may be similarly prepared, with an azithromycin/swellable material core, coated by a porous or porosigen-containing membrane.

As it is an object of this invention is to reduce the exposure of the upper GI tract to high concentrations of azithromycin, a fifth especially preferred class of dosage forms includes those forms which incorporate a delay before the onset of sustained release of azithromycin. An exemplary embodiment can be illustrated by a tablet comprising a core containing azithromycin coated with a first coating of a polymeric material of the type useful for sustained release of azithromycin and a second coating of the type useful for delaying release of drugs when the dosage form is ingested. The first coating is applied over and surrounds the tablet. The second coating is applied over and surrounds the first coating.

The tablet can be prepared by techniques well known in the art and contains a therapeutically useful amount of azithromycin plus such excipients as are necessary to form the tablet by such techniques.

The first coating may be a sustained release coating as known in the art, especially polymer coatings, to fabricate the membrane, as previously discussed for reservoir systems. Suitable and preferred polymer coating materials, equipment, and coating methods also include those previously discussed.

Materials useful for preparing the second coating on the tablet include polymers known in the art as enteric coatings for delayed-release of pharmaceuticals. These most commonly are pH-sensitive materials such as cellulose acetate phthalate, cellulose acetate trimellitate, hydroxypropyl methyl cellulose phthalate, poly (vinyl acetate phthalate), and acrylic copolymers such as Eudragit L-100 (Röhm Pharma) and related materials, as more fully detailed below under "Delayed Release". The thickness of the delayed-release coating is adjusted to give the desired delay property. In general, thicker coatings are more resistant to erosion and, consequently, yield a longer delay. Preferred coatings range from about 300 µm in thickness to about 3 mm in thickness.

When ingested, the twice-coated tablet passes through the stomach, where the second coating prevents release of the azithromycin under the acidic conditions prevalent there. When the tablet passes out of the stomach and into the small intestine, where the pH is higher, the second coating erodes or dissolves according to the physicochemical properties of the chosen material. Upon erosion or dissolution of the second coating, the first coating prevents immediate or rapid release of the azithromycin and modulates the release so as to prevent the production of high concentrations, thereby minimizing side-effects.

A further preferred embodiment comprises a multiparticulate wherein each particle is dual coated as described above for tablets, first with a polymer designed to yield sustained release of the azithromycin and then coated with a polymer designed to delay onset of release in the environment of the GI tract when the dosage form is ingested. The beads contain azithromycin and may contain one or more excipients as needed for fabrication and performance. Multiparticulates which contain a high fraction of azithromycin relative to binder are preferred. The multiparticulate may be of composition and be fabricated by any of the techniques previously disclosed for multiparticulates used to make reservoir systems (including extrusion and spheronization, wet granulation, fluid bed granulation, and rotary bed granulation seed building, and so forth).

The sustained release coating may be as known in the art, especially polymer coatings, to fabricate the membrane, as previously discussed for reservoir systems. Suitable and preferred polymer coating materials, equipment, and coating methods also include those previously discussed.

The rate of azithromycin release from the sustained-release-coated multiparticulates (i.e., the multiparticulates before they receive the delayed-release coating) and methods of modifying the coating are also controlled by the factors previously discussed for reservoir system azithromycin multiparticulates.

The second membrane or coating for dual coated multiparticulates is a delayed-release coating which is applied over the first sustained-release coating, as disclosed above for tablets, and may be formed from the same materials. It should be noted that the use of the so-called "enteric" materials to practice this embodiment differs significantly from their use to produce conventional enteric dosage forms. With conventional enteric forms, the object is to delay release of the drug until the dosage form has passed the stomach and then to to deliver the dose in the duodenum. Dosing of azithromycin directly and completely to the duodenum is undesirable, however, due to the side effects sought to be minimized or avoided by this invention. Therefore, if conventional enteric polymers are to be used to practice this embodiment, it may be necessary to apply them significantly more thickly than in conventional practice, in order to delay drug release until the dosage form reaches the lower GI tract. However, it is preferred to effect a sustained or controlled delivery of azithromycin after the delayed-release coating has dissolved or eroded, therefore the benefits of this embodiment may be realized with a proper combination of delayed-release character with sustained-release character, and the delayed-release part alone may or may not necessarily conform to USP enteric criteria. The thickness of the delayed-release coating is adjusted to give the desired delay property. In general, thicker coatings are more resistant to erosion and, consequently, yield a longer delay.

Delayed Release

A first delayed release embodiment according to the invention is a "pH-dependent coated tablet", which comprises a tablet core comprising azithromycin, a disintegrant, a lubricant, and one or more pharmaceutical carriers, such core being coated with a material, preferably a polymer, which is substantially insoluble and impermeable at the pH of the stomach, and which is more soluble and permeable at the pH of the small intestine. Preferably, the coating polymer is substantially insoluble and impermeable at pH<5.0, and water-soluble at pH>5.0. It is also preferred that the tablet core be coated with an amount of polymer sufficient to assure that substantially no release of azithromycin from the dosage form occurs until the dosage form has exited the stomach and has resided in the small intestine for about 15 minutes or greater, preferably about 30 minutes or greater, thus assuring that minimal azithromycin is released in the duodenum. Mixtures of a pH-sensitive polymer with a water-insoluble polymer may also be employed. Tablets are coated with an amount of polymer comprising from about 10% to about 80% of the weight of the azithromycin-containing tablet core. Preferred tablets are coated with an amount of polymer comprising about 15% to about 50% of the weight of the azithromycin tablet core.

pH-sensitive polymers which are relatively insoluble and impermeable at the pH of the stomach, but which are more soluble and permeable at the pH of the small intestine and colon include polyacrylamides, phthalate derivatives such as acid phthalates of carbohydrates, amylose acetate phthalate, cellulose acetate phthalate, other cellulose ester phthalates, cellulose ether phthalates, hydroxypropylcellulose phthalate, hydroxypropylethylcellulose phthalate, hydroxypropylmethylcellulose phthalate, methylcellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinylacetate phthalate copolymer, styrene and maleic acid copolymers, polyacrylic acid derivatives such as acrylic acid and acrylic ester copolymers, polymethacrylic acid and esters thereof, poly acrylic methacrylic acid copolymers, shellac, and vinyl acetate and crotonic acid copolymers.

Preferred pH-sensitive polymers include shellac; phthalate derivatives, particularly cellulose acetate phthalate, polyvinylacetate phthalate, and hydroxypropylmethylcellulose phthalate; polyacrylic acid derivatives, particularly polymethyl methacrylate blended with acrylic acid and acrylic ester copolymers; and vinyl acetate and crotonic acid copolymers.

Cellulose acetate phthalate (CAP) may be applied to azithromycin tablets to provide delayed release of azithromycin until the azithromycin-containing tablet has passed the sensitive duodenal region, that is to delay the release of azithromycin in the gastrointestinal tract until about 15 minutes, and preferably about 30 minutes, after the azithromycin-containing tablet has passed from the stomach to the duodenum. The CAP coating solution may also contain one or more plasticizers, such as diethyl phthalate, polyethyleneglycol-400, triacetin, triacetin citrate, propylene glycol, and others as known in the art. Preferred plasticizers are diethyl phthalate and triacetin. The CAP coating formulation may also contain one or more emulsifiers, such as polysorbate-80.

Anionic acrylic copolymers of methacrylic acid and methylmethacrylate are also particularly useful coating materials for delaying the release of azithromycin from azithromycin-containing tablets until the tablets have moved to a position in the small intestine which is distal to the duodenum. Copolymers of this type are available from RöhmPharma Corp, under the tradenames Eudragit-L® and Eudragit-S®. Eudragit-L® and Eudragit-S® are anionic copolymers of methacrylic acid and methylmethacrylate. The ratio of free carboxyl groups to the esters is approximately 1:1 in Eudragit-L® and approximately 1:2 in Eudragit-S®. Mixtures of Eudragit-L® and Eudragit-S® may also be used. For coating of azithromycin-containing tablets, these acrylic coating polymers must be dissolved in an organic solvent or mixture of organic solvents. Useful solvents for this purpose are acetone, isopropyl alcohol, and methylene chloride. It is generally advisable to include 5–20% placticizer in coating formulations of acrylic copolymers. Useful plasticizers are polyethylene glycols, propylene glycols, diethyl phthalate, dibutyl phthalate, castor oil, and triacetin.

The delay time before release of azithromycin, after the "pH-dependent coated tablet" dosage form has exited the stomach, may be controlled by choice of the relative amounts of Eudragit-L® and Eudragit-S® in the coating, and by choice of the coating thickness. Eudragit-L® films dissolve above pH 6.0, and Eudragit-S® films dissolve above 7.0, and mixtures dissolve at intermediate pH's. Since the pH of the duodenum is approximately 6.0 and the pH of the colon is approximately 7.0, coatings composed of mixtures of Eudragit-L® and Eudragit-S® provide protection of the duodenum from azithromycin. If it is desired to delay release of azithromycin until the azithromycin-containing "pH-dependent coated tablet" has reached the colon, Eudragit-S® may be used as the coating material, as described by Dew et al (Br. J. Clin. Pharmac. 14 (1982) 405–408). In order to delay the release of azithromycin for about 15 minutes or more, preferably 30 minutes or more, after the dosage form has exited the stomach, preferred coatings comprise from about 9:1 to about 1:9 Eudragit-L®/Eudragit-S®, more preferably from about 9:1. to about 1:4 Eudragit-L®/Eudragit-S®. The coating may comprise from about 3% to about 70% of the weight of the uncoated tablet core. Preferably, the coating comprises from about 5% to about 50% of the weight of the tablet core.

In a further embodiment, a "pH-dependent coated bead", beads (about 0.5 to 3.0 mm in diameter) comprising azithromycin plus carrier are coated with one or more of the aforementioned pH-sensive polymers. The coated beads may be placed in a capsule or may be compressed into a tablet, with care taken to avoid damaging the polymeric coat on individual beads during tablet compression. Preferred coated beads are those which exhibit substantially no release of azithromycin from the dosage form until the beads have exited the stomach and have resided in the small intestine for about 15 minutes or greater, preferably about 30 minutes or greater, thus assuring that minimal azithromycin is the duodenum. Mixtures of a pH-sensitive polymer with a water-insoluble polymer are also included. As described above, azithromycin-containing beads may be coated with mixtures of polymers whose solubilities vary at different pH's. For example preferred coatings comprise from about 9:1 to about 1:9 Eudragit-L®/Eudragit-S®, more preferably from 9:1 to 1:4 Eudragit-L®/Eudragit-S®. The coating may comprise from about 5% to about 200% of the weight of the uncoated bead core. Preferably, the coating comprises from about 10% to about 100% of the weight of the bead core.

In a further embodiment, ("pH-dependent coated particle"), small azithromycin-containing particles (about 0.01 to 0.5 mm in diameter, preferably 0.05 to 0.5 mm in diameter) are coated with one or more of the aforementioned pH-sensitive polymers. The coated particles may be placed in a capsule or may be compressed into a table, with care taken to avoid damaging the polymeric coat on individual particles during tablet compression. Preferred coated particles are those which exhibit substantially no release of azithromycin from the dosage form until the particles have exited the stomach and have resided in the small intestine for about 15 minutes or greater, preferably 30 minutes or greater, thus assuring that minimal azithromycin is released in the duodenum. Mixtures of a pH-sensitive polymer with a water-insoluble polymer are also included. Preferred azithromycin-containing particles are coated with an amount of polymer comprising about 25% to about 200% of the weight of the uncoated azithromycin-containing particle core.

A further embodiment constitutes a modification of the pH-dependent coated tablet, pH-dependent coated bead, and pH-dependent coated particle embodiments. The azithromycin-containing core tablet, bead, or particle is first coated with a barrier coat, and then is coated with the pH-dependent coat. The function of the barrier coat is to separate azithromycin from the pH-dependent coat. Since azithromycin is a base, hydration of the azithromycin in the core may serve to raise the pH in the microenvironment of the pH-dependent coating, thus prematurely initiating the permeabilization or dissolution of the pH-dependent coating, resulting in premature release of some or all of the azithromycin dose in the stomach or duodenum. Suitable barrier coatings are composed of water-soluble materials such as sugars such as sucrose, or water-soluble polymers such as hydroxypropyl cellulose, hydroxypropyl methylcellulose, and the like. Hydroxypropyl cellulose and hydroxypropylmethylcellulose are preferred. The barrier coat may comprise from about 1% to about 15%, preferably from about 2% to about 10%, of the weight of the uncoated azithromycin-containing tablet, bead or particle core.

Coating of azithromycin-containing tablets, beads and particles may be carried out using equipment known in the art. For example, azithromycin-containing tablet cores may be coated with a pan-coater, such as a Hi-Coater (Freund Corp.), or an Accela-Cota (Manesty Corp., Liverpool). Azithromycin-containing beads and particles are preferably coated using a fluidized bed coater, such as a Wurster coater, utilizing coating equipment available for example from the Glatt Corporation (Ramsey, N.J.). Beads may also be coated using a rotary granulator, such as a CF-granulator available from Freund Corp.

In a further embodiment ("bursting osmotic core device"), azithromycin is incorporated in an osmotic bursting device which comprises a tablet core or bead core containing azithromycin and, optionally, one or more osmagents. Devices of this type have been generally disclosed in Baker, U.S. Pat. No. 3,952,741, which is incorporated herein by reference. Examples of osmagents are sugars such as glucose, sucrose, mannitol, lactose, and the like; and salts such as sodium chloride, potassium chloride, sodium carbonate, and the like; water soluble acids such as tartaric acid, fumaric acid, and the like. The azithromycin-containing tablet core or bead core is coated with a polymer which forms a semipermeable membrane, that is, a membrane which is permeable to water but is substantially impermeable to azithromycin. Examples of polymers which provide a semipermeable membrane are cellulose acetate, cellulose acetate butyrate, and ethylcellulose, preferably cellulose acetate. The semipermeable coating membrane may alternatively be composed of one or more waxes, such as insect and animal waxes such as beeswax, and vegetable waxes such as carnauba wax and hydrogenated vegetable oils. A melt mixture of a polyethylene glycol, e.g., polyethylene glycol-6000, and a hydrogenated oil, e.g., hydrogenated castor oil, may be used as a coating, as described for isoniazid tablets by Yashino (Capsugel Symposia Series; Current Status on Targeted Drug Delivery to the Gastrointestinal Tract; 1993; pp.185–190). Preferred semipermeable coating materials are cellulose esters and cellulose ethers, polyacrylic acid derivatives such as polyacrylates and polyacrylate esters, and polyvinyl alcohols and polyalkenes such as ethylene vinyl alcohol copolymer. Especially preferred semipermeable coating materials are cellulose acetate and cellulose acetate, butyrate.

When a coated tablet or bead of the "bursting osmotic core" embodiment of this invention is placed in an aqueous environment of use, water passes through the semipermeable membrane into the core, dissolving a portion of the azithromycin and osmagent, generating a colloidal osmotic pressure which results in bursting of the semipermeable membrane and release of azithromycin into the aqueous environment. By choice of bead or tablet core size and geometry, identity and quantity of osmagent, and thickness of the semipermeable membrane, the time lag between placement of the dosage form into the aqueous environment of use and release of the enclosed azithromycin may be chosen. It will be appreciated by those skilled in the art that increasing the surface-to-volume ratio of the dosage form, and increasing the osmotic activity of the osmagent serve to decrease the time lag, whereas increasing the thickness of the coating will increase the time lag. Preferred osmotic-bursting devices of this invention are those which exhibit substantially no release of azithromycin from the dosage form until the dosage form has exited the stomach and has resided in the small intestine for about 15 minutes or greater, preferably about 30 minutes or greater, thus assuring that minimal azithromycin is released in the duodenum. A bursting osmotic core tablet or bead has a tablet or bead core which may contain from about 25–95% azithromycin, about 0–60% osmagent, as described above, and about 5–20% other pharmaceutical aids such as binders and lubricants. The semipermeable membrane coating on a tablet, preferably a cellulose acetate coating, is present at a weight corresponding to from about 2% to about 30%, preferably from about 3% to about 10%, of the weight of the tablet core. The semipermeable membrane coating on a bead, preferably a cellulose acetate coating, is present at a weight corresponding to from about 2% to about 80%, preferably from 3% to 30%, of the weight of the bead core.

A bursting osmotic core device possesses no mechanism for "sensing" that the device has exited the stomach and entered the duodenum. Thus devices of this type release azithromycin at a predetermined time after entering an aqueous environment, i.e., after being swallowed. In the fasted state, indigestible non-disintegrating solids, such as the "bursting osmotic core devices" of this invention, are emptied from the stomach during phase III of the Interdigestive Migrating Myoelectric Complex (IMMC), which occurs approximately every 2 hr in the human. Depending on the stage of the IMMC at the time of dosing in the fasted state, a bursting osmotic core device may exit the stomach almost immediately after dosing, or as long as 2 hr after dosing. In the fed state, indigestible non-disintegrating solids, which are <11 mm in diameter, will empty slowly from the stomach with the contents of the meal (Khosla and Davis, Int. J. Pharmaceut. 62 (1990) R9–R 11). If the indigestible non-disintegrating solid is greater than about 11 mm in diameter, i.e., about the size of a typical tablet, it will be retained in the duodenum during phase III of an IMMC, after the entire meal has been digested and has exited the stomach. It is preferred to delay the release of azithromycin until about 15 min or more, preferably 30 minutes or more, after the dosage form has exited the stomach. A bursting osmotic core device which releases azithromycin about 1.5 hr after ingestion will decrease the incidence and severity of gastrointestinal side effects in a population of patients administered azithromycin in such devices. A preferred bursting osmotic core device starts to release azithromycin at about 2.5 hr after entering an aqueous environment, i.e., after ingestion, to more reliably assure that the device releases its azithromycin distal to the duodenum, when dosed in the fasted state. A more preferred "bursting osmotic core device" will start to release azithromycin at about 4 hr after entering an aqueous environment. This 4 hr delay permits dosing in the fed state, and allows for an about 3.5 hr retention in the fed stomach, followed by an approximately 30 minute delay after the dosage form has exited from the stomach. In this way, the release of azithromycin into the most sensitive portion of the gastrointestinal tract, the duodenum, is minimized.

In a further embodiment, a "bursting coated swelling core", an azithromycin-containing tablet or bead is prepared which also comprises 25–70% of a swellable material, such as a swellable colloid (e.g., gelatin), as described in Milosovich, U.S. Pat. No. 3,247,066, incorporated herein by reference. Preferred swelling core material are hydrogels, i.e., hydrophilic polymers which take up water and swell, such as polyethylene oxides, polyacrylic acid derivatives such as polymethyl methacrylate, polyacrylamides, polyvinyl alcohol poly-N-vinyl-2-pyrrolidone, carboxymethylcellulose, starches, and the like. Preferred swelling hydrogels for this embodiment are polyethylene oxides and carboxymethylcellulose. The colloid/hydrogel-containing azithromycin-containing core tablet or bead is coated, at least in part, by a semipermeable membrane. Examples of polymers which provide a semipermeable membrane are cellulose acetate and cellulose acetate butyrate,and ethylcellulose, preferably cellulose acetate. The semipermeable coating membrane may alternatively be composed of one or more waxes, such as insect and animal waxes such as beeswax, and vegetable waxes such as carnauba wax, and hydrogenated vegetable oils. A melt mixture of a polyethylene glycol, e.g., polyethylene glycol-6000, and a hydrogenated oil, e.g., hydrogenated castor oil, may be used as a coating, as described for isoniazid tablets by Yoshino (Capsugel Symposia Series; Current Status on Targeted Drug Delivery to the Gastrointestinal Tract; 1993; pp.185–190). Preferred semipermeable coating materials are cellulose esters and cellulose ethers, polyacrylic acid derivatives such as polyacrylates and polyacrylate esters, and polyvinyl alcohols and polyalkenes such as ethylene vinyl alcohol copolymer. Especially preferred semipermeable coating materials are cellulose acetate and cellulose acetate butyrate.

When a coated tablet or bead having a bursting coated swelling core is placed in an aqueous environment of use, water passes through the semipermeable membrane into the core, swelling the core and resulting in bursting of the semipermeable membrane and release of azithromycin into the aqueous environment. By choice of bead or tablet core size and geometry, identity and quantity of swelling agent, and thickness of the semipermeable membrane, the time lag between placement of the dosage form into the aqueous environment of use and release of the enclosed azithromycin may be chosen. Preferred bursting coated swelling core devices of this invention are those which exhibit substantially no release of azithromycin from the dosage form until the dosage form has exited the stomach and has resided in the small intestine for about 15 minutes or greater, preferably about 30 minutes or greater, thus assuring that minimal azithromycin is released in the duodenum.

A bursting coated swelling core tablet or bead has a tablet or bead core which may contain from about 25–75% azithromycin; about 15–60% swelling material, e.g., hydrogel; about 0–15% optional osmagent; and about 5–20% other pharmaceutical aids such as binders and lubricants. The semipermeable membrane coating on a tablet, preferably a cellulose acetate coating, is present at a weight corresponding to from about 2% to about 30%, preferably from 3% to 10%, of the weight of the tablet core. The semipermeable membrane coating on a bead, preferably a cellulose, acetate coating, is present at a weight corresponding to from about 2% to about 80%, preferably from 3% to 30%, of the weight of the bead core.

A bursting coated swelling core device possesses no mechanism for sensing that the device has exited the stomach and entered the duodenum. Thus devices of this type release their azithromycin contents at a predetermined time after entering an aqueous environment, i.e., after being swallowed, as previously discussed for bursting osmotic core devices, and the same consideration and preferences apply to making bursting coated swelling core devices.

In a further embodiment, a "pH-triggered osmotic bursting device", azithromycin is incorporated into a device of the type described in allowed commonly assigned co-pending U.S. Pat. No. 5,358,502, issued Oct. 25, 1994, incorporated herein by reference. The device comprises azithromycin and optionally one or more osmagents, surrounded at least in part by a semipermeable membrane. The semipermeable membrane is permeable water and substantially impermeable to azithromycin and osmagent. Useful osmagents are the same as those described above for bursting osmotic core devices. Useful semipermeable membrane materials are the same as those described above for bursting osmotic core devices. A pH-trigger means is attached to the semipermeable membrane. The pH-trigger means is activated by a pH above 5.0, and triggers the sudden delivery of the azithromycin. In this embodiment, the pH-trigger means comprises a membrane or polymer coating which surrounds the semipermeable coating. The pH-trigger coating contains a polymer which is substantially impermeable and insoluble in the pH range of the stomach, but becomes permeable and soluble at about the pH of the duodenum, about pH 6.0.

Exemplary pH-sensitive polymers are polyacrylamides, phthalate derivatives such as acid phthalates of carbohydrates, amylose acetate phthalate, cellulose acetate phthalate, other cellulose ester phthalates, cellulose ether phthalates, hydroxypropylcellulose phthalate, hydroxypropylethylcellulose phthalate, hydroxypropylmethylcellulose phthalate, methylcellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinylacetate phthalate copolymer, styrene and maleic acid copolymers, polyacrylic acid derivatives such as acrylic acid and acrylic ester copolymers, polymethacrylic acid and esters thereof, poly acrylic methacrylic acid copolymers, shellac, and vinyl acetate and crotonic acid copolymers.

Preferred pH-sensitive polymers include shellac; phthalate derivatives, particularly cellulose acetate phthalate, polyvinylacetate phthalate, and hydroxypropylmethylcellulose phthalate; polyacrylic acid derivatives, particularly polymethyl methacrylate blended with acrylic acid and acrylic ester copolymers; and vinyl acetate and crotonic acid copolymers. As described above cellulose acetate phthalate is available as a latex under the tradename Aquateric® (registered trademark of FMC Corp., Philadelphia, Pa.), and acrylic copolymers are available under the tradenames Eudragit-R® and Eudragit-L®. For approriate application in this embodiment, these polymers should be plasticized utilizing plasticizers described above. The pH-trigger coating may also comprise a mixture of polymers, for example cellulose acetate and cellulose acetate phthalate. Another suitable mixture comprises Eudragit-L® and Eudragit-S®; the ratio of the two, and the coating thickness, defining the sensitivity of the "trigger", i.e., the pH at which the outer pH-trigger coating weakens or dissolves.

A pH-triggered osmotic bursting device generally operates as follows. After oral ingestion, the pH-trigger coating, which surrounds the semi-permeable coating, which in turn surrounds the azithromycin-containing core tablet or bead, remains undissolved and intact in the stomach. In the stomach, water may or may not commence penetration through the pH-trigger coating and the semipermeable coating, thus starting hydration of the core, which contains azithromycin and optional osmagent. After the device has exited the stomach and has entered the small intestine, the pH-trigger coating rapidly disintegrates and dissolves, and water passes through the semipermeable coating, dissolving azithromycin and optional osmagent within the core. As the colloidal osmotic pressure across the semipermeable coating exceeds some threshold value, the semipermeable coating fails, and the device bursts, releasing azithromycin. It is preferred that this bursting and release of azithromycin occur at about 15 minutes or more, preferably 30 minutes or more, after the pH-triggered osmotic bursting device exits the stomach and enters the duodenum, thus minimizing exposure of the sensitive duodenum to azithromycin.

For a pH-triggered osmotic bursting device, the lag-time or delay-time is controlled by the choice and amount of osmagent in the core, by the choice of semipermeable coating, and by the thickness of the semipermeable coating. It will be appreciated by those skilled in the art, for example, that a thicker semipermeable coating will result in a longer delay after the device has exited the stomach. A preferred pH-triggered osmotic bursting device is a bead or tablet core of azithromycin with optional osmagent, coated with a 3–20% by weight cellulose acetate membrane, coated with a 3–20% by weight membrane composed of about 1:1 cellulose acetate/cellulose acetate phthalate. Another preferred pH-triggered osmotic bursting device is a bead or tablet core of azithromycin with optional osmagent, coated with a 3–20% by weight cellulose acetate membrane, coated with a 3–20% by weight membrane comprising from about 9:1 to about 1:1 Eudragit-L®/Eudragit-S®.

Advantageously, because a pH-triggered osmotic bursting device possesses a mechanism for sensing that the device has exited the stomach, interpatient variability in gastric emptying is not significant.

In a further embodiment, a "pH-triggered bursting coated swelling core", a tablet core or bead containing azithromycin and a swelling material is coated with a semipermeable coating which is further coated with a pH-sensitive coating. The core composition, including choice of swelling material is as described above for the bursting coated swelling core embodiment. The choice of semipermeable coating material and pH-sensitive coating material are as described above for the "pH-triggered osmotic core" embodiment. This device is described in detail in commonly-assigned copending U.S. patent application Ser. No. 08/023,227, filed Feb. 25, 1993, incorporated herein by reference.

A pH-triggered bursting swelling core embodiment generally operates as follows. After oral ingestion, the pH-trigger coating, which surrounds the semi-permeable coating which in turn surrounds the azithromycin-containing core tablet or bead, remains undissolved and intact in thee stomach. In the stomach, water may or may not commence penetration through the pH-trigger coating and the semipermeable coating, thus starting hydration of the core, which contains azithromycin and water-swelling material, preferably a hydrogel. When the pH-triggered bursting swelling core device exits the stomach and enters the small intestine, the pH-trigger coating rapidly disintegrates and dissolves; and water passes through the semipermeable coating, dissolving azithromycin and swelling the water-swellable material within the core. As the swelling pressure across the semipermeable coating exceeds some threshold value, the semipermeable coating fails, and the device bursts, releasing azithromycin. It is preferred that this bursting and release of azithromycin occur at about 15 minutes or more, preferably about 30 minutes, after the pH-triggered bursting swelling core device exits the stomach and enters the duodenum, thus minimizing exposure of the sensitive duodenum to azithromycin.

For the "pH-triggered bursting swelling core" device, the lag-time or delay-time can be controlled by the choice and amount of swelling material in the core, by the choice of semipermeable coating, and by the thickness of the semipermeable coating. It will be appreciated by those skilled in the art, for example, that a thicker semipermeable coating will result in a longer delay after the device has exited the stomach. A preferred pH-triggered bursting swelling core device contains a bead or tablet core of azithromycin with synthetic hydrogel, preferably carboxymethylcellulose, coated with a 3–20% by weight cellulose acetate membrane, coated with a 3–20% by weight membrane composed of about 1:1 cellulose acetate/cellulose acetate phthalate. Another preferred pH-triggered bursting swelling core device contains a bead or tablet core of azithromycin with synthetic hydrogel, preferably carboxymethylcellulose, coated with a 3–20% by weight cellulose acetate membrane, coated with a 3–20% by weight membrane composed of from about 9:1 to about 1:1 Eudragit-L®/Eudragit-S®.

Advantageously, because the a pH-triggered bursting swelling core device possesses a mechanism for sensing that the device has exited the stomach, interpatient variability in gastric emptying is not significant.

In a further embodiment, an "enzyme-triggered supported liquid membrane device" comprises azithromycin formulated in a dosage form of the type described in International Application PCT/ US93/07463, published as WO 94/12159 on Jun. 9, 1994, herein incorporated by reference. This embodiment generally has the form of a tablet or bead containing azithromycin and excipients, a microporous hydrophobic support membrane that at least partially surrounds the beneficial agent, and a hydrophobic liquid entrained within the pores of the support membrane. Alternatively, the azithromycin and excipients may be incorporated into a capsule shell which comprises a microporous hydrophobic membrane with a hydrophobic liquid entrained within the pores of the capsule shell. The hydrophobic liquid is substantially impermeable to both the aqueous environment and the azithromycin tablet or bead core formulation. The hydrophobic liquid is capable of change such that it becomes substantially permeable to the aqueous environment or azithromycin formulation. After ingestion of this embodiment by a mammal, including a human, azithromycin release into the gastrointestinal system is delayed until about 15 minutes or more, preferably about 30 minutes, after the dosage form has exited the stomach and moved into the duodenum.

In an azithromycin enzyme-triggered supported liquid membrane device, the supported hydrophobic liquid is preferably a liquid which undergoes change which is enzymatically catalyzed in the lumen of the small intestine, and not in the stomach. Exemplary hydrophobic liquids are triglycerides, fatty anhydrides, fatty acid esters of cholesterol, hydrophobic amino acid esters, and the like. Preferred triglycerides include triolein, tricaprylin, trilaurin, olive oil, palm oil, coconut oil, sesame seed oil, corn oil, peanut oil, soybean oil, and this like. Preferred fatty acid anhydrides include caprylic anhydride, lauric anhydride, myristic anhydride and the like. Mixtures of hydrophobic liquids may be used. Exemplary materials for the microporous hydrophobic support membrane include cellulose esters, polycarbonates, polyalkenes, polystyrenes, polyvinyl esters, polysiloxanes, polyacrylates, and polyethers. Preferably the hydrophobic microporous membrane with entrained hydrophobic liquid is impermeable to azithromycin, until gastrointestinal enzymes have catalyzed a change in the hydrophobic oil, as described below.

In the environment of use, i.e., the small intestinal lumen, lipases and esterases degrade the aforementioned hydrophobic oils, releasing surfactant products in the pores of the microporous membrane of this embodiment, thus producing aqueous channels through which the azithromycin in the device core may exit through the microporous hydrophobic support membrane. Release of the azithromycin may occur by simple diffusion, osmotic pumping, osmotic bursting, or by bursting due to the presence of a swellable material, e.g., hydrogel, in the azithromycin-containing core of the device.

In an azithromycin enzyme-triggered supported liquid membrane device, hydrophobic oils is may be used which are substrates for small intestinal proteases such as carboxypeptidase and chymotrypsin. Exemplary oil are hydrophobic esters of amino acid derivatives.

In a further embodiment, a "bacterially degradable coating device", azithromycin-containing tablets or beads are coated with a material which is substantially impermeable to azithromycin in the stomach and small intestine, the coating material undergoing degradation by bacteria or by bacterially-released enzymes (e.g., azo reductases) in the colon, thus releasing azithromycin. Upon degradation of the coating material in the colon, azithromycin is released. Embodiments of this design minimize exposure of the sensitive upper (duodenal) region of the small intestine to azithromycin. Examples of coating materials of this embodiment are polymers from ethylenically unsaturated monomers, crosslinked by a substituted or unsubstituted divinylazobenzene, as described in U.S. Pat. Nos. 4,663,308 and 5,032,572, each herein incorporated by reference. Other examples of coating materials of this embodiment are degradable polysaccharides such as pectin and alginin, and mixtures of these degradable polysaccharides with film-forming polymers such as ethylcellulose, methylcellulose, hydroxypropylmethylcellulose, and the like. Polysaccharide coatings of this type have been disclosed in Depascali et al, EP-485840; in Roehr and Steinicke, DD-296840; and in Ashford and Fell, Capsugel Symposia Series; Current Status on Targeted Drug Delivery to the Gastrointestinal Tract; 1993; pp. 133–142.

Examples of a bacterially degradable coating device include a bead or tablet core which contain about 25–90% azithromycin with additional tabletting aids such as binders and lubricants, coated with an azo-polymer or polysaccharide membrane whose weight corresponds to from about 5–80%, preferably 10–50% of the weight of the tablet or bead core.

In a further embodiment, a "swelling plug device", azithromycin and appropriate excipients and carriers are incorporated into a non-dissolving capsule-half which is sealed at one end by a hydrogel plug. This hydrogel plug swells in an aqueous environment, and, after swelling for a predetermined time, exits the capsule thus opening a port through which the azithromycin can leave the capsule and be delivered to the aqueous environment. Preferred hydrogel-plugged capsules are those which exhibit substantially no release of azithromycin from the dosage form until the dosage form has exited the stomach and has resided in the small intestine for about 15 minutes or greater, preferably about 30 minutes or greater, thus assuring that minimal azithromycin is released in the duodenum. Hydrogel-plugged capsules of this type have been described in patent application WO-90/19168, which is incorporated herein by reference. An azithromycin swelling plug device may be prepared by loading azithromycin into a non-dissolving half-capsule shell which may be formed from a wide variety of materials, including but not limited to polyethylene, polypropylene, poly(methylmethacrylate), polyvinylchloride, polystyrene, polyurethanes, polytetrafluoroethylene, nylons, polyformaldehydes, polyesters, cellulose acetate, and nitrocellulose. The open end of the capsule shell is then "plugged" with a cylindrical plug formed from a hydrogel-forming material, including but not limited to, a horo- or co-poly(alkylene oxide) crosslinked by reaction with isocyanate or unsaturated cyclic ether groups, as described in PCT Application WO 90/09168. The composition and length of the hydrogel "plug" is selected to minimize release of azithromycin to the stomach and duodenum, to decrease the incidence and/or severity of gastrointestinal side effects. The plugged capsule-half is finally sealed with a water-soluble, e.g., gelatin, capsule-half placed over the hydrogel-plugged end of the azithromycin-containing non-dissolving capsule-half. In a preferred embodiment of the "swelling plug device", the sealed device is coated with a "pH-sensitive enteric polymer or polymer mixture", for example cellulose acetate phthalate or copolymers of methacrylic acid and methylmethacrylate. The weight of the enteric polymer coat will generally be from 2–20%, preferably from 4–15% of the weight of the uncoated sealed capsule. When this preferred "enteric-coated swelling plug device" is ingested orally, the enteric coat prevents release azithromycin in the stomach. The enteric coat dissolves quickly, e.g., within about 15 minutes, in the duodenum, triggering swelling of the hydrogel plug, exiting of the hydrogel plug, and release of the incorporated azithromycin into the gastrointestinal tract at a time greater than about 15 minutes after, and preferably greater than about 30 minutes after, the dosage form has passed from the stomach into the duodenum. Prototype unfilled "swelling plug devices" may be obtained from Scherer DDS Limited, Clydebank, Scotland, under the designation "Pulsincap™".

It will be appreciated by those skilled in the art that the various coated azithromycin tablet, bead and particle embodiments described above can be coated using standard coating equipment, such as pan coaters (e.g., Hi-Coater available from Freund Corp; Accela-Cota available from Manesty, Liverpool); fluidized bed coaters, e.g., Wurster coaters, (available from Glatt Corp, Ramsey, N.J. and Aeromatic Corp., Columbia, Md.), and rotary granulators, e.g.

CF-Granulator (available from Freund Corp). Core tablets are made on standard tablet presses, such as a Killian press. Azithromycin containing beads and particles are made in fluidized bed granulators, rotary granulators, and extruder/spheronizers.

Delayed release embodiments of the invention are solid dosage forms for oral administration comprising azithromycin and a pharmaceutically acceptable carrier, which release not more than 10% of their incorporated azithromycin into a mammal's stomach, and which release not more than an additional 10% during the first 15 minutes after entering said mammal's duodenum. The timing of release of azithromycin in the stomach or duodenum may be tested utilizing a variety of approaches including, but not limited to, x-ray evaluation, nuclear magnetic resonance imaging, gamma scintigraphy, or direct sampling of the gastric and duodenal contents via intubation. These tests, while possible, can be very difficult to carry out in humans. A more convenient test for a delayed release embodiment of the current invention is a two stage in vitro dissolution test, which incorporates a 15 minute test of azithromycin release in a simulated gastric fluid, and a 15 minute test of azithromycin release in a simulated intestinal fluid. This two stage in vitro test for a delayed release dosage form is described in more detail below. For certain delayed release embodiments described in this disclosure, release of azithromycin is "triggered" by the presence of pancreatic lipase in the duodenum. For in vitro evaluation of lipase-triggered delayed release dosage forms, 5 mg/ml porcine pancreatic lipase (Sigma Chem., St. Louis, Mo.) is included in the dissolution medium for the second stage of the dissolution test.

The invention will now be illustrated by the following examples which are not to be taken as limiting. In general, the examples demonstrate the incidence of gastrointestinal side-effects upon oral, IV, duodenal, and ileal-cecal dosing of azithromycin and the preparation of controlled-release dosage forms of azithromycin within the scope of this invention.

In the examples which follow, the following definitions and tests have been employed:

1. "Q" is used to designate a quantity of azithromycin either in mg or in percent (%), as indicated. The Q is associated with a time or "pull point" at which an indicated aliquot of solution was removed for assay of azithromycin, the time of removal or pull point being indicated in hours as a subscript. Thus, a "$Q_{0.25}$" of 15 mg means that 15 mg of azithromycin was dissolved in one quarter hour.

2. Specification of a quantity in percent (%) means percent by weight based on total weight, unless otherwise indicated.

3. "Eudragit®" is the registered trademark of Röhm Pharma GmbH, Germany for a family of enteric polymeric methacrylates.

4. "Opadry®" is the registered trademark of Colorcon Inc., West Point, Pa. for a family of plasticized cellulose ethers which include hydroxypropyl methylcellulose, hydroxypropyl cellulose and methylcellulose that are supplied as powders for reconstitution in water.

5. "Surelease®" is the registered trademark of Colorcon Inc., West Point, Pa. for an aqueous, fully plasticized polymeric dispersion of ethylcellulose.

6. "mgA" is an abbreviation for "milligrams of active azithromycin". For example, "250 mg A" means 250 mg of active azithromycin".

7. "X mgA of multiparticulate" (where X is a number) means the amount of multiparticulate containing X mgA. For example, "250 mgA of multiparticulate" means the weight of multiparticulate containing 250 mgA.

8. "mgAm" is an abbreviation for "mgA of multiparticulate".

9. "Use environment" means the aqueous environment of the gastrointestinal tract.

10. In Vitro Dissolution Tests The following two in vitro tests can be used to screen sustained release and delayed release embodiments of this invention for in vivo suitability. If a particular dosage form satisfies the criteria disclosed below for either test, it is within the scope of the invention.

Sustained Release Dosage Test: Sustained release dosage forms of azithromycin are tested in a standard USP rotating paddle apparatus as disclosed in United States Pharmacopoeia XXIII (USP) Dissolution Test Chapter 711, Apparatus 2. Paddles are rotated at 50 rpm and the dissolution test is conducted in, as the test medium, 900 mL of pH 0.1 mg/mL of the enzyme trypsin must be added to the buffer. At indicated times following test initiation (i.e., insertion of the dosage form into the analyzed for azithromycin by high performance liquid chromatography (HPLC) as disclosed below. Dissolution results are reported as mg azithromycin dissolved versus time. Sustained release dosage forms that meet the following criteria are within the scope of the invention: (1) $Q_{0.25} \leq 200$ mg azithromycin dissolved; (2) $Q_1 \leq 500$ mg azithromycin dissolved; (3) $Q_2 \leq 1000$ mg azithromycin dissolved; (4) $Q_4 \leq 1,500$ mg azithromycin dissolved; and (5) $Q_6 \leq 2000$ mg azithromycin dissolved, where Q is as defined above.

Delayed Release Dosage Test: Delayed release dosage forms of azithromycin are also tested in a standard USP rotating paddle apparatus as specified above. The test is modified from that given above. Paddles are rotated at 50 rpm and dissolution is conducted in two stages at 37° C. A first acid stage is implemented by inserting a delayed release dosage form into 750 mL of 0.1N HCl acid media. At 15 minutes, a filtered aliquot of test acid media is analyzed for azithromycin content by HPLC. A second stage is implemented immediately following the first stage by adding 250 mL of 0.2M tribasic sodium phosphate buffer, thereby converting the acid media from the first stage to a buffer having a pH of about 6.8. If the measured pH is plus or minus more than 0.05 pH units from 6.8, it should be suitably adjusted by adding alkali metal hydroxide or hydrochloric acid (each typically 2N), as appropriate. At 15 minutes after addition of phosphate buffer, a second filtered aliquot of test medium is analyzed for azithromycin content by HPLC. Dissolution results are reported as % azithromycin dissolved versus time. Delayed release dosage forms that meet the following criteria are within the scope of the invention: (1) $Q_{0.25} < 10\%$ azithromycin dissolved; and (2) $Q_{0.5} < Q_{0.25} + 10\%$ azithromycin dissolved. The test is reliable for dosage forms containing up to 7,000 mgA.

The criteria in each test are also referred to in the Examples as "dissolution criteria".

11. HPLC Quantification: When conducting either of the in vitro dissolution tests described above, azithromycin is quantified by reverse-phase high performance liquid chromatography and electrochemical detection as follows. An aliquot of test solution is filtered to remove particulates and diluted to a target concentration of approximately 3 µg/mL. A fixed volume of 50 µL is injected onto a pre-column (5 cm×4.6 mm diameter) with a 5 micron spherical alumina (80 Å diameter pores) based hydrocarbonaceous stationary phase (Gamma. RP-1, ES Industries, Berlin, N.J.). The pre-column is followed by a 15 cm×4.6 mm diameter column containing the same stationary phase. The chromatography system is substantially as described in Shepard et al., J. Chromatography, 565: 321–337 (1991). An isocratic mobile phase consisting of 72% 0.02M potassium phosphate monobasic buffer and 28% acetonitrile (v/v, final pH of 11) is employed at a flow rate of 1.5 mL/min. The electrochemical detector employs dual glassy carbon electrodes (Model LC-4B amperometric detector Bioanalytical Systems, West Lafayette, Ind.) operating in the oxidative screen mode with the reference electrode set at about +0.7 V and the working electrode, set at about +0.8 V. In sustained-release test media, actual quantification of azithromycin is effected by comparison of sample chromatogram peak height ratio relative to diphenhydramine internal standard against an azithromycin standard chromatogram peak height ratio also relative to the same internal standard. In delayed-release (acid) test media, because azithromycin can hydrolyze in acid media to desosaminylazithromycin, the amount of dissolved azithromycin which had hydrolyzed is determined and converted to its equivalent as azithromycin (conversion factor, 1.26). In delayed-release test media, diphenhydramine is again employed as an internal peak height reference standard for both sample and azithromycin/desosaminylazithromycin standard chromatograms.

12. Where no value is given in the Tables, it was not determined.

EXAMPLE 1

This example demonstrates that a 2 g oral dose of azithromycin gives a similar incidence of gastrointestinal side effects, whether the 2 g is given as a single oral dose or as eight 250 mg doses, given as 250 mg every half-hour for 3.5 hr.

In a double-blind, randomized, placebo-controlled parallel group study, healthy male subjects were divided into three groups. Group A received a single 2 g azithromycin dose as eight 250 mg azithromycin capsules ("bolus dosing" group). Group B received the same total dose, administered as eight 250 mg capsules at the rate of one 250 mg capsule each 30 minutes for 3.5 hr ("divided dosing" group). Group C received matching placebo capsules. All subjects received eight capsules of drug or placebo at time 0, and a capsule of drug or placebo every half-hour for 3.5 hr. All subjects were dosed after an overnight fast. Blood samples were withdrawn prior to dosing, and at 0.5, 1, 1.5, 2, 2.5, 3, 3.5, 4, 6, 8, 12, 16, 24, 48, 72, 96, 144, 192, and 240 hr post-dosing. Serum azithromycin concentrations were determined using the high performance liquid chromatography assay described in Shepard et al., J. Chromatography, 565: 321–337 (1991). Total systemic exposure to azithromycin was determined by measuring the area under the serum azithromycin concentration vs. time curve (AUC) for each subject in, a given group, and then by calculating a mean AUC for the group. Cmax is the highest serum azithromycin concentration achieved in a subject. Tmax is the time at which Cmax is achieved. Serum pharmacokinetic data for this example are presented in Table I.

Prior to dosing and each blood sampling time, each subject filled out a questionnaire, which consisted of a series of "Visual Analogue Scales" in which the subject was required to rate, on a scale of 0–10, the severity of certain potential side effects. The subjects were instructed that "0" indicated an absent effect and "10" indicated the worst possible effect. The subjects were instructed to interpolate between 0 and 10 for moderate side effects.

A total of 45 subjects completed this study: 16 on placebo, 15 on 2 g single dose, and 14 on 250 mg dose every half-hour for 3.5 hours. For four side effects evaluated at 20 time points, a total of 3600 individual visual-analogue-scale evaluations were obtained.

Analysis of side effect visual-analogue-scale data was carried out in two formats. In the first format (Table II), the analysis concentrated on the general incidence of side effects of a particular type. For each side effect type (e.g., abdominal pain), Table II reports the number of subjects who reported a score >1 at any time during the 240 hr post-dosing, and the number of subjects who reported a score >4 at any time during the 240 hr post-dosing. This analysis assumes that all scores >1 represent a real side effect occurrence, however mild or severe. A score >4 is presumed to reflect a moderate-to-severe side effect occurrence.

In the second format (Table III), the analysis reflects the general severity and duration of side effects. For a particular side effect (e.g., Abdominal Pain) in a particular subject, all visual-analogue-scale scores (over the 240 hr post-dose period) were summed to give a "cumulative score" over the entire time period of evaluation. "Cumulative scores" for all members of a treatment group were summed, and divided by the number of subjects in the group, to give a Mean Cumulative Score. The scale of this Mean Cumulative Score does not correspond to the original 0–10 scale, since it reflects the summation of all non-zero scores over the entire evaluation period. Table III presents Mean Cumulative Scores for abdominal pain, nausea, regurgitation, and abdominal cramping.

Table I demonstrates that the total systemic azithromycin exposure of the two dosing groups, reflected in the AUC, was similar. For the divided dosing group, Cmax was lower and Tmax was longer, as expected because the dosing took place over 3.5 hr, rather than in a single bolus dose.

Table II demonstrates that abdominal pain, nausea, and abdominal cramping were frequent side effects for a 2 g bolus dose, while regurgitation was not. Divided dosing over 3.5 hr gave a similar side effect incidence profile. Table III demonstrates that the overall severity of azithromycin-induced side effects was similar for the bolus-dosing and divided dosing treatments.

The data presented in Table II and Table III demonstrate that delivering a 2 g dose at a rate of 500 mg/hr does not result in a greatly improved side effect incidence, compared with a single 2 g bolus dose. The manner in which the divided dose was administered in this example resulted in exposure of the upper gastrointestinal tract, i.e., the stomach and duodenum, to the entire divided dose.

TABLE I

Azithromycin Pharmacokinetics For A 2 g Dose given as a Single Dose, or as Eight 250 mg doses every Half-Hour for 3.5 Hours (mean values).

| TREATMENT | Cmax (μg/ml) | Tmax (hr) | $AUC_{0-144}$ (μg-hr/ml) |
|---|---|---|---|
| 2 g single dose | 1.69 | 1.3 | 18.8 |
| 250 Mg per half-hr for 3.5 hr | 1.13 | 4.4 | 18.9 |

TABLE II

Incidence of Visual-Analogue-Scale scores exceeding 1 or 4 at any time during the 240 hour post-dose evaluation period, for the side effects abdominal pain, nausea, regurgitation, and abdominal cramping. Compares 2 g bolus dose vs. eight 250 mg capsules dosed every half-hr for 3.5 hr.

| TREATMENT | Abdominal Pain | | Nausea | | Regurgitation | | Abdominal Cramping | |
|---|---|---|---|---|---|---|---|---|
| | >1 | >4 | >1 | >4 | >1 | >4 | >1 | >4 |
| Placebo | 0/16 | 0/16 | 0/16 | 0/16 | 0/16 | 0/16 | 0/16 | 1/16 |
| 2 g single dose | 6/15 | 2/15 | 2/15 | 1/15 | 0/15 | 0/15 | 6/15 | 1/15 |
| 250 mg per half-hr for 3.5 hr | 6/14 | 1/14 | 3/14 | 0/14 | 0/14 | 0/14 | 4/14 | 0/14 |

Note: Results reported as (#patients reporting score)/(total # patients).

TABLE III

MEAN CUMULATIVE SCORE
Mean Cumulative Visual Analogue Scale Data for the Side Effects Abdominal Pain, Nausea, Regurgitation, and Abdominal Cramping, over the entire 240 hour post-dose evaluation period. See text for explanation of "mean cumulative score".

| TREATMENT | n* | Abdominal Pain | Nausea | Regurgitation | Abdominal Cramping |
|---|---|---|---|---|---|
| Placebo | 16 | 0.19 | 0.25 | 0.06 | 1.19 |
| 2 g Single Dose | 15 | 6.4 | 1.93 | 0.53 | 4.67 |
| 250 Mg/half-hr for 3.5 hr | 13 | 6.31 | 2.77 | 1.38 | 4.46 |

*number of subjects averaged

EXAMPLE 2

This example demonstrates that dosing of 2 g azithromycin directly to the human duodenum results in a higher incidence and severity of gastrointestinal side effects than observed when azithromycin (2 g) is dosed directly to the ileocecal region of the small intestine. This example supports the conclusion that the incidence and severity of azithromycin gastrointestinal side effects can be reduced by decreasing the exposure of the duodenum to orally dosed azithromycin. This example also demonstrates that direct delivery of azithromycin to the duodenum or the ileocecal region of the small intestine does not result in any loss of systemic bioavailability, relative to oral dosing.

Healthy male subjects were divided into two groups. Group A received a 2 g azithromycin dose administered directly into the duodenum as a solution via a nasoenteric tube. Group B received the same azithromycin solution dose, administered directly into the ileocecal region of the small intestine via a nasoenteric tube. The nasoenteric tube was a single lumen, 4.5 meter tube with a side port for delivery of drug. Placement of the tube for duodenal and ileocecal delivery was confirmed by fluoroscopy. Infusions to the duodenum or ileocecal region were administered at a concentration of 40 mg/ml within 5 minutes. All subjects were dosed after an overnight fast. Subjects were randomized to receive azithromycin and placebo via nasoenteric tube and intravenous infusion in a double-blind, placebo controlled fashion. Two weeks later, subjects were crossed over to the alternate route of active drug administration.

Blood samples were withdrawn prior to dosing, and at 0.08, 0.17, 0.33, 0.66, 1, 2, 4, 8, 12, 24, 48, 72, and 96 hr post-dosing. Serum azithromycin concentrations were determined using the high performance liquid chromatography assay described in Shepard et al., J. Chromatography, 565: 321–337, (1991). Total systemic exposure to azithromycin was determined by measuring the area under the serum azithromycin concentration vs. time curve (AUC) for each subject in a given group, and then by calculating a mean AUC for the group. Cmax is the highest serum azithromycin concentration achieved in a subject. Tmax is the time at which Cmax is achieved. Serum pharmacokinetic data for this example are presented in Table IV. In one leg of this study, all subjects received an intravenous 2g azithromycin dose. The intravenous AUC was determined in order to calculate the absolute duodenal and ileocecal bioavailabilities, as described below.

Prior to dosing and each blood sampling time, each subject filled out a questionnaire, which consisted of a series of "Visual Analogue Scales" in which the subject was required to rate, on a scale of 0–10, the severity of certain potential side effects. The subjects were instructed that "0" indicated an absent effect and "10" indicated the worst possible effect. The subjects were instructed to interpolate between 0 and 10 for moderate side effects.

A total of 11 subjects completed this study: 5 on duodenal dosing and 6 on ileocecal dosing. For four side effects evaluated at 14 time points, a total of 616 individual visual-analogue-scale evaluations were obtained.

Analysis of side effect visual-analogue-scale data was carried out in two formats. In the first format (Table V), the analysis concentrated on the general incidence of side effects of a particular type. For each side effect type (e.g., abdominal pain), Table V reports the number of subjects who reported a score >1 at any time during the 96 hr post-dosing, and the number of subjects who reported a score >4 at any time during the 96 hr post-dosing. This analysis assumes that all scores >1 represent a real side effect occurrence, however mild or severe. A score >4 is presumed to reflect a moderate-to-severe side effect occurrence.

In the second format (Table VI), the analysis reflects the general severity and duration of side effects. For a particular side effect (e.g., Abdominal Pain) in a particular subject, all visual-analogue-scale scores (over the 96 hr post-dose period) were summed to give a "cumulative score" over the entire time period of evaluation. "Cumulative scores" for all members of a treatment group were summed, and divided by the number of subjects in the group, to give a Mean Cumulative Score. The scale of this Mean Cumulative Score does not correspond to the original 0–10 scale, since it reflects the summation of all non-zero scores over the entire evaluation period. Table VI presents Mean Cumulative Scores for abdominal pain, nausea, regurgitation, and abdominal cramping.

Table IV demonstrates that the absorption of a duodenally administered solution dose of azithromycin is fast, as evidenced by a short Tmax of 0.3 hr, and a high Cmax. Ileocecal dosing resulted in slower absorption, with a measured Tmax (1.39 hr) which is similar to the Tmax observed for oral capsule dosing in Example 1 (1.3 hr; Table I). The overall systemic exposure to drug (AUC) was 15% lower for ileocecal dosing compared with duodenal dosing. When compared to intravenous dosing in the same subjects, the bioavailability for duodenal dosing was 43.8%, and the bioavailability for ileocecal dosing was 39.1%; where bioavailability, e.g., duodenal bioavailability, is defined as $AUC_{duodenal}/AUC_{IV} \times 100$. The bioavailability of the duodenal azithromycin solution was slightly larger than the oral bioavailability of an azithromycin capsule, which is typically about 38%. The bioavailability of the ileocecal azithromycin solution was similar to that of an orally dosed capsule.

Table V (same format as Table II) demonstrates that the incidence of gastrointestinal side effects is generally higher for duodenal dosing than for ileocecal dosing. Table VI demonstrates that the overall severity of gastrointestinal side effects was higher for duodenal dosing than for ileocecal dosing.

TABLE IV

Azithromycin Pharmacokinetics for a 2 g Solution Dose administered to the duodenal (n = 5) or ileocecal (n = 6) region of the small intestine via nasoenteric tube (mean values).

| TREATMENT | Cmax (μm/ml) | Tmax (hr) | AUC$_{0-96}$ (μg · hr/ml) |
|---|---|---|---|
| Duodenal | 3.24 | 0.3 | 17.0 |
| Ileocecal | 0.77 | 1.39 | 14.5 |

TABLE V

Incidence of Visual-Analogue-Scale scores exceeding 1 or 4 at any time during the 96 hour post-dose evaluation period, for the side effects abdominal pain, nausea, regurgitation, and abdominal cramping. Compares 2 g azithromycin administration directly into the duodenal (n = 5) and ileocecal (n = 6) regions of the small intestine.

| TREAT-MENT | ABDOMINAL PAIN | | NAUSEA | | REGURGI-TATION | | ABDOMINAL CRAMPING | |
|---|---|---|---|---|---|---|---|---|
| | >1 | >4 | >1 | >4 | >1 | >4 | >1 | >4 |
| Duodenal | 4/5 | 0/5 | 2/5 | 1/5 | 3/5 | 0/5 | 5/5 | 0/5 |
| Ileo-cecal | 2/6 | 0/6 | 2/6 | 0/6 | 0/6 | 0/6 | 2/6 | 0/6 |

TABLE VI

MEAN CUMULATIVE SCORE
Mean Cumulative Visual Analogue Scale Data for the Side Effects Abdominal Pain, Nausea, Regurgitation, and Abdominal Cramping, over the entire 96 hour post-dose evaluation period. See text for explanation of "mean cumulative score". Dosing of a 2 g azithromycin solution was directly into the duodenal or ileocecal regions of the small intestine.

| TREATMENT | n* | Abdominal Pain | Nausea | Regurgi-tation | Abdominal Cramping |
|---|---|---|---|---|---|
| Duodenal | 5 | 13.4 | 11.6 | 7.2 | 13.2 |
| Ileocecal | 6 | 2.7 | 2.0 | 0 | 3.3 |

*number of subjects averaged

EXAMPLE 3

This example demonstrates that, when azithromycin is dosed intravenously, the incidence and severity of gastrointestinal side effects is low, compared with the incidence and severity of gastrointestinal side effects resulting from oral dosing at an equivalent dose. These observations support the conclusion that the gastrointestinal side effects of orally dosed azithromycin are locally mediated in the gastrointestinal tract by direct contact between the orally dosed drug and the intestinal wall, and do not result primarily from effects related to the presence of azithromycin in the systemic circulation.

Healthy male subjects were divided into four groups. Group A received a 2 hr intravenous infusion of a placebo solution (0 g azithromycin). Group B received a 2 hr intravenous infusion of a 1 g dose of azithromycin. Group C received a 2 hr intravenous infusion of a 2 g dose of azithromycin. Group D received a 2 hr intravenous infusion of a 4 g dose of azithromycin. Based on an oral bioavailability of 37%, these intravenous doses of 0, 1, 2 and 4 g are equivalent to oral doses of 0, 2.7, 5.4, and 10.8 g, respectively. All subjects were dosed after an overnight fast.

Blood samples were withdrawn prior to dosing, and at 0.25, 0.5, 0.75, 1; 1.5, 2, 4, 8, 12, 18, 24, 72, 96, 144, 192, and 240 hr post-dosing. Serum azithromycin concentrations were determined using the high performance liquid chromatography assay described in Shepard et al., J. Chromatography, 565: 321–337 (1991). Total systemic exposure to azithromycin was determined by measuring the area under the serum azithromycin concentration vs. time curve (AUC) for each subject in a given group, and then by calculating a mean AUC for the group. Cmax is the highest serum azithromycin concentration achieved in a subject. Tmax is the time at which Cmax is achieved. Serum pharmacokinetic data for this example are presented in Table VII.

Prior to dosing and each blood sampling time, each subject filled out a questionnaire, which consisted of a series of "Visual Analogue Scales" in which the subject was required to rate, on a scale of 0–10, the severity of certain potential side effects. The subjects were instructed that "0" indicated an absent effect and "10" indicated the worst possible effect. The subjects were instructed to interpolate between 0 and 10 for moderate side effects.

A total of 22 subjects completed this study: 5 on placebo, 6 at 1 g azithromycin total dose, 6 at 2 g azithromycin total dose, and 5 at 4 g azithromycin total dose. For four side effects evaluated at 18 time points, a total of 1,584 individual visual-analogue-scale evaluations were obtained.

Analysis of side effect visual-analogue-scale data was carried out in two formats. In the first format (Table VIII), the analysis concentrated on the general incidence of side effects of a particular type. For each side effect type (e.g., abdominal pain), Table VIII reports the number of subjects who reported a score >1 at any time during the 240 hr post-dosing, and the number of subjects who reported a score >4 at any time during the 240 hr post-dosing. This analysis assumes that all scores >4 represent a real side effect occurrence, however mild or severe. A score >4 is presumed to reflect a moderate-to-severe side effect occurrence.

In the second format (Table IX), the analysis reflects the general severity and duration of side effects. For a particular side effect (e.g., Abdominal Pain) in a particular subject, all visual-analogue-scale scores (over the 240 hr post-dose period) were summed to give a "cumulative score" over the entire time period of evaluation. "Cumulative scores" for all members of a treatment group were summed, and divided by the number of subjects in the group, to a give a Mean Cumulative Score. The scale of this Mean Cumulative Score does not correspond to the original 0–10 scale, since it reflects the summation of all non-zero scores over the entire evaluation period. Table IX presents Mean Cumulative Scores for abdominal pain, nausea, regurgitation, and abdominal cramping.

Table VII presents pharmacokinetic data for the intravenous azithromycin dosing of this example. Comparison with Table 1 of Example 1 demonstrates that intravenous dosing of azithromycin results in higher systemic exposure than does oral dosing. For example, a 2 g intravenous dose gives an AUC of 45.6 µg-hr/ml (Table VII), while a 2 g oral dose gives an AUC of 18.8 µg-hr/ml (Table 1). Thus, for the purpose of comparing gastrointestinal side effects of orally and intravenously administered azithromycin, it is generally appropriate to compare a 2 g oral dose with a 1 g intravenous dose. In fact, the systemic drug exposure achieved by a 1 g intravenous dose (AUC=23.4 µg-hr/ml) is more than the systemic drug exposure provided by a 2 g oral dose (AUC=18.8 µhr/ml).

Table VIII (same format as Table II) demonstrates that the incidences of abdominal pain, nausea, regurgitation, and abdominal cramping were low after a 2 hr intravenous infusion of 1.0 g azithromycin. Comparison of this data with side effect incidence data for a 2 g oral azithromycin dose (which gives approximately the same systemic azithromycin exposure) (see Table II) demonstrates that, for approximately the same degree of systemic drug exposure, oral dosing causes a much higher incidence of side effects. These observations indicate that the gastrointestinal side effects of orally dosed azithromycin do not primarily result from exposure of the systemic circulation to the drug, but instead most likely result from direct exposure of the intestinal wall to the drug.

Table VIII also indicates that, at higher intravenous azithromycin doses, e.g., 2.0 g, gastrointestinal side effects occur. A 2.0 g intravenous azithromycin dose is equivalent to a 5.4 g oral azithromycin dose, from the standpoint of equivalent systemic drug exposure. At an even higher intravenous dose, a higher side effect incidence is observed. While GI side effects can be elicited by high intravenous doses, these observations are consistent with the statement that azithromycin GI side effects are mediated by direct contact of the drug with the intestinal wall in the lumen, based upon the following additional study. Twelve ileostomy subjects were administered an IV infusion of 500 mg azithromycin over 1 hr. Serum was collected predose and at 0.17, 0.33, 0.5, 1, 2, 4, 8, 12, 24, 48, 72, 96, 120, and 144 hr following initiation, of the infusion. In addition, the contents of the subjects' ileostomy bags were collected for the following intervals: 12 hr predose, 0–6 hr post-dose, 6–12 hr post-dose, and 12–24 hr post-dose. The serum and ileostomy fluid concentrations of azithromycin were assayed. In the 24 hr following an IV azithromycin dose, 13% of the dose was recovered intact in the ileostomy fluid indicated that IV-administered azithromycin enters the lumen of the small intestine, probably via biliary excretion and/or transintestinal elimination. Thus it is not surprising that high intravenous doses of azithromycin can cause gastrointestinal side effects, since a portion of the IV dose partitions into the lumen of the small intestine.

Table IX demonstrates that the overall severity of gastrointestinal side effects resulting from a 1.0 g intravenous dose is low, and, is lower than that observed for a 2 g oral dose (compare with Table III). Based on an oral bioavailability of 37%, these intravenous doses are equivalent to oral doses of 0, 2.7, 5.4 and 10.8 g, respectively. At higher IV doses (e.g., 4 g) gastrointestinal side effects are observed. However, it is likely that these GI side effects are due to partitioning of the IV dose into the lumen of the small intestine, as clearly demonstrated above in the ileostomy study.

TABLE VII

Azithromycin Pharmacokinetics: For a 2 hr infusion of 1 g (n = 6) or 2 g (n = 6) or 4 g (n = 5) total dose.

| TOTAL IV DOSE (g) | EQUIVALENT ORAL DOSE* (g) | $C_{max}$ (µg/ml) | $T_{max}$ (hr) | $AUC_{0-inf}$ (µg-hr/ml) |
|---|---|---|---|---|
| 1.0 | 2.7 | 3.11 | 1.9 | 23.4 |
| 2.0 | 5.4 | 6.84 | 1.8 | 45.6 |
| 4.0 | 10.8 | 9.91 | 1.1 | 82.1 |

*Calculated by dividing the IV dose by the oral bioavailability of azithromycin (0.37)

TABLE VIII

Incidence of Visual-Analogue-Scale scores exceeding 1 or 4 at any time during the 240 hour post-dose evaluation period, for the side effects abdominal pain, nausea, regurgitation, and abdominal cramping. Compares intravenous doses of 0 g (placebo), 1 g, 2 g, and 4 g azithromycin, infused over a 2 hr period. Based on an oral bioavailability of 37%, these intravenous doses are equivalent to oral doses of 0, 2.7, and 5.4 g, respectively. Reported incidences for the 1.0, 2.0 and 4.0 g doses have not been corrected for placebo effects.

| IV DOSE | Abdominal Pain | | Nausea | | Regurgitation | | Abdominal Cramping | |
|---|---|---|---|---|---|---|---|---|
|  | >1 | >4 | >1 | >4 | >1 | >4 | >1 | >4 |
| 0 g | 2/5 | 0/5 | 1/5 | 0/5 | 0/5 | 0/5 | 1/5 | 0/5 |
| 1 g | 1/5 | 0/5 | 0/5 | 0/5 | 0/5 | 0/5 | 0/5 | 0/5 |
| 2 g | 2/6 | 1/6 | 4/6 | 2/6 | 1/6 | 0/6 | 1/6 | 1/6 |
| 4 g | 4/5 | 0/5 | 3/5 | 2/5 | 1/5 | 1/5 | 4/5 | 2/5 |

TABLE IX

MEAN CUMULATIVE SCORE
Mean Cumulative Visual Analogue Scale Data for the Side Effects Abdominal Pain, Nausea, Regurgitation, and Abdominal Cramping, over the entire 240 hour post-dose evaluation period. See text for explanation of "mean cumulative score". Azithromycin was dosed intravenously at a total dose of 0 g (placebo), 1 g, 2 g, or 4 g. Based on an oral bioavailability of 37%, these intravenous doses are equivalent to oral doses of 0, 2.7, 5.4, and 10.8 g, respectively. Mean cumulative scores for 1.0, 2.0 and 4.0 g doses have not been corrected for placebo effects.

| IV DOSE (g) | n* | Abdominal Pain | Nausea | Regurgitation | Abdominal Cramping |
|---|---|---|---|---|---|
| 0 | 5 | 8.8 | 3.2 | 2.6 | 3.4 |
| 1.0 | 6 | 1.5 | 0 | 0 | 0.5 |
| 2.0 | 6 | 5.7 | 13.2 | 0.5 | 3.8 |
| 4.0 | 5 | 12.8 | 10.6 | 3.8 | 11.8 |

*number of subjects averaged

EXAMPLE 4

This example illustrates a process for making a sustained release azithromycin multiparticulate membrane-moderated reservoir which releases azithromycin at different rates depending on coating thickness of a diffusion barrier coating. The process comprised (1) preparing uncoated azithromycin multiparticulate cores; and (2) applying a diffusion barrier coating over the cores. This example further illustrates the in vitro sustained release dosage test procedure for evaluating dissolution and release of azithromycin from the dosage form.

Azithromycin-containing multiparticulate cores were prepared by blending azithromycin with microcrystalline cellulose (Avicel® PH101, FMC Corp., Philadelphia, Pa.) in relative amounts of 95:5 (w/w), wet massing the blend in a Hobart mixer with water equivalent to approximately 27% of the weight of the blend, extruding the wet mass through a perforated plate (Luwa EXKS-1 extruder, Fuji Paudal Co.,Osaka Japan), spheronizing the extrudate (Luwa QJ-230 marumerizer, Fuji Paudal Co.) and drying the final cores which were about 1 mm diameter. The final sustained release beads were made by coating over the particle cores with a plasticized ethylcellulose dispersion (Surelease®, Colorcon, West Point, Pa., typically applied at 15% solids concentration). For example 4A (about 100 g batch size), final coating was conducted in a bottom spray Wurster fluid bed coater (Aeromatic Strea-1, Niro Inc., Bubendorf, Switzerland). For examples 4B, 4C and 4D (about 1 kg batch sizes), final coating was conducted in a rotary granulator (CF-360 granulator, Freund Indust., Tokyo, Japan). The amount of coating applied was varied to obtain different dissolution rate behavior. Example 4A had an additional coating of 2% Opadry® over the 13% Surelease® Coat.

Finished sustained release multiparticulates were tested using the in vitro sustained release dosage test procedure previously described and the results are presented in Table 4-1. Example 4D was tested as 1,500 mgA multiparticulate and examples 4A through 4C were tested as 250 mgA multiparticulate in a capsule. Examples 4A through 4D satisfy the in vitro sustained release dissolution criteria and are sustained release embodiments within the scope of the invention.

TABLE 4-1

| Example | Surelease ® Coating (%) | In Vitro Sustained Release Dissolution Criteria $Q_{0.25} \leq$ 200 $Q_{0.25}$ mgA | $Q_1 \leq$ 500 $Q_1$ mgA | $Q_2 \leq$ 1,000 $Q_2$ mgA | $Q_4 \leq$ 1,500 $Q_4$ mgA | $Q_6 \leq$ 2,000 $Q_6$ mgA | Initial Dose Tested (mgA) |
|---|---|---|---|---|---|---|---|
| 4A | 13.0 2.0 Opadry ® | 0 | 9 | 44 | 104 | 175 | 250 |
| 4B | 11.1 | 4 | 33 | 113 | 144 | 154 | 250 |
| 4C | 13.0 | 0 | 18 | 35 | 50 | 83 | 250 |
| 4D | 13.0 | 38 | 128 | 252 | 465 | 641 | 1500 |

EXAMPLE 5

This example illustrates using temporal criteria in conjunction with in vitro dissolution test results to design a dosage form, such as a sachet, which exhibits a desired dissolution profile.

Using the in vitro dissolution test results from Example 4B, it is desired to make a sustained release dosage form. Using the temporal criteria and the corresponding data of Example 4B, a maximum scaled mgA of multiparticulate was calculated for each individual temporal criterion, and set forth in Table 5-1.

TABLE 5-1

MAXIMUM SCALED DOSE

| Temporal Criteria | Example 4B Dissolution Results | Maximum Scaled mgA of multiparticulate |
|---|---|---|
| ≦200 mgA in 15 min. | 4 mgA in 15 min. | 12,500 mgAm |
| ≦500 mgA in 1 hr. | 33 mgA in 1 hr. | 3,788 mgAm |
| ≦1,000 mgA in 2 hr. | 113 mgA in 2 hr. | 2,212 mgAm |

TABLE 5-1-continued

MAXIMUM SCALED DOSE

| Temporal Criteria | Example 4B Dissolution Results | Maximum Scaled mgA of multiparticulate |
|---|---|---|
| ≦1,500 mgA in 4 hr. | 144 mgA in 4 hr. | 2,604 mgAm |
| ≦2,000 mgA in 6 hr. | 154 mgA in 6 hr. | 3,247 mgAm |

Each maximum scaled value was calculated by scaling up the results of Example 4B to yield the highest value consistent with the corresponding temporal criterion. For instance the maximum scaled value at 15 minutes (12,500 mgAm) was calculated as 200 mgA×(250 mgAm÷4 mgA), where the 250 mgAm corresponds to the, initial dose tested. The maximum scaled value at 2 hr (2,212 mgAm) was similarly calculated as 1000 mgA×(250 mgAm÷113 mgA).

Table 5-1 indicates that the maximum scaled dose of Example 4B multiparticulate which should be used to make a dosage form within the scope of the invention is 2,212 mgAm, the minimum of the maximum scaled values calculated.

Maximum scaled doses were also calculated using the temporal criteria together with the data of Examples 4A, 4C, and 4D in the same manner as above. Table 5-2 summarizes the maximum scaled dose for Examples 4A through 4D.

TABLE 5-2

MAXIMUM SCALED DOSE

| Example | Maximum Scaled Dose of Sustained Release Multiparticulate |
|---|---|
| 4A | 2,857 mgA |
| 4B | 2,212 mgA |
| 4C | 6,024 mgA |
| 4D | 4,680 mgA |

EXAMPLE 6

This example illustrates using weight criteria in conjunction with in vitro dissolution test results to custom design a dosage form tailored for an animal of a given body weight. The data of example 4B are employed to calculate the minimum body weight for each of the weight criteria.

TABLE 6-1

MAXIMUM DOSE FOR A GIVEN BODY WEIGHT

| Weight Criteria | Example 4B Dissolution Results | Maximum Scaled mgA of multiparticulate for 100 kg body weight |
|---|---|---|
| ≦4 mg/kg in 15 min. | 4 mgA in 15 min. | 25,000 mgAm |
| ≦10 mg/kg in 1 hr. | 33 mgA in 1 hr. | 7,576 mgAm |
| ≦20 mg/kg in 2 hr. | 113 mgA in 2 hr. | 4,425 mgAm |
| ≦30 mg/kg in 4 hr. | 144 mgA in 4 hr. | 5,208 mgAm |
| ≦40 mgA/kg in 6 hr. | 154 mgA in 6 hr. | 6,494 mgAm |

Each maximum scaled value was calculated by scaling up, to a 100 kg animal weight, the results of Example 4B to yield the highest value consistent with the corresponding weight criterion. For instance, the maximum scaled value at 15 minutes (25,000 mgAm) was calculated as: 4 mg/kg×100 kg×(250 mgAm÷4 mgA), where the 250 mgAm corresponds to the initial dose tested. The maximum scaled value at 2 hr was similarly 20 mg/kg×100 kg×(250 mgAm÷113 mgA).

Table 6-1 indicates that the maximum scaled dose of multiparticulate which should be used to make a dosage form within the scope of the invention is 4,425 mgAm, the minimum of the calculated scaled values.

In the same manner as above, Table 6-2 lists the calculated maximum amounts of sustained release multiparticulate for Examples 4A, 4B, 4C, and 4D which should be employed for a given body weight of 100 kg to make a dosage form within the scope of the invention.

TABLE 6-2

Maximum Dose Deliverable To A Given Body Weight

| Example | Maximum Dose Sustained Release Multiparticulate 100 kg Body Weight |
|---|---|
| 4A | 5,714 mgAm |
| 4B | 4,425 mgAm |
| 4C | 12,048 mgAm |
| 4D | 9,360 mgAm |

EXAMPLE 7

This example illustrates using the weight criteria in conjunction with in vitro dissolution test results to determine the minimum animal body weight with which a sustained release dosage form should be used.

A sustained release sachet containing 2000 mgAm is made with the multiparticulate of Example 4B. A minimum animal body weight was calculated for use with this sachet according to each of the weight criteria.

TABLE 7-1

Minimum Body Weights

| Weight Criteria | Example 4B Dissolution Results | Minimum Scaled Body Weight for use with 2,000 mgAm |
|---|---|---|
| ≦4 mg/kg In 15 min. | 4 mgA In 15 min. | 8 kg |
| ≦10 mg/kg In 1 hr. | 33 mgA In 1 hr. | 26.4 kg |
| ≦20 mg/kg In 2 hr. | 113 mgA In 2 hr. | 45.2 kg |
| ≦30 mg/kg In 4 hr. | 144 mgA In 4 hr. | 38.4 kg |
| ≦40 mgA/kg In 6 hr. | 154 mgA In 6 hr. | 30.8 kg |

Each minimum scaled body weight was calculated by using the data of Example 4B and assuming a 2000 mgAm to calculate the smallest weight consistent with each individual corresponding weight criterion. For instance the scaled value at 15 minutes (8 kg) was calculated as: 2000 mgAm×(4 mgA/250 mgAm)÷(4 mgA/kg). The maximum scaled value at 2 hr (45.2 kg) was similarly calculated as: 2000 mgAm×(113 mgA/250 mgAm)÷(20 mgA/kg).

Table 7-1 indicates the minimum body weight to which a sachet containing 2000 mgAm of Example 4B should be administered is 45.2 kg, the maximum of the calculated scaled body weights.

Minimum scaled body weights were also calculated using the weight criteria together with the dissolution data of Examples 4A, 4C, and 4D in the same manner as above. Table 7-2 summarizes the minimum body weight for 250 mgAm and 2000 mgAm total doses of Examples 4A, 4B, 4C and 4D, to make a dosage within the scope of the invention.

TABLE 7-2

Minimum Body Weight At Given Dose

| Example | Minimum Body Weight per 250 mgA Sustained Release Multiparticulate | Minimum Body Weight per 2000 mgA Sustained Release Multiparticulate |
|---|---|---|
| 4A | 4.4 kg | 35.0 kg |
| 4B | 5.7 kg | 45.2 kg |
| 4C | 2.1 kg | 16.6 kg |
| 4D | 2.7 kg | 21.4 kg |

EXAMPLE 8

This example illustrates a process for making sustained release azithromycin multiparticulate membrane-moderated reservoir systems which release azithromycin at different rates depending on coating thickness of a diffusion barrier coating. The process comprised applying a diffusion barrier coating directly to an azithromycin multiparticulate. This example further evaluates, by the in vitro sustained release dosage test, the release profile.

Azithromycin-containing multiparticulates were prepared by loading 1,000 g azithromycin compound directly into a rotary granulator/coater (Freund CF-360 granulator). Then, a plasticized ethylcellulose (Surelease®) coating suspension diluted to 15% solids was sprayed onto the rotating bed of azithromycin particles. During spray application, both agglomeration of azithromycin particles into larger particles and coating of these agglomerates with the diffusion barrier membrane occurred. In some examples, a water soluble coating of Opadry® (typically diluted to 10% solids for spraying) was applied over the barrier membrane as added protection.

Finished sustained release multiparticulates were tested using the in vitro sustained release dosage test procedure previously described and the results are presented in Table 8-1. Examples 8A through 8G satisfy the in vitro sustained release dissolution criteria and are sustained release embodiments of the invention.

TABLE 8-1

| Example No. (Mean Particle Size. μm) | Surelease ® Coating (%) | In Vitro Sustained Release Dissolution Criteria | | | | | |
|---|---|---|---|---|---|---|---|
| | | $Q_{0.25} \leq$ 200 $Q_{0.25}$ mgA | $Q_1 \leq$ 500 $Q_1$ mgA | $Q_2 \leq$ 1000 $Q_2$ mgA | $Q_4 \leq$ 1500 $Q_4$ mgA | $Q_6 \leq$ 2000 $Q_6$ mgA | Initial Dose Tested mgAm |
| 8A (240 μm) | 16.7 | — | 110 | 206 | 216 | 228 | 228 |
| 8B (240 μm) | 16.6[1] 0.5 Opadry ® | — | 191 | — | 196 | — | 250 |

TABLE 8-1-continued

| Example No. (Mean Particle Size. μm) | Surelease ® Coating (%) | $Q_{0.25} \leq$ 200 $Q_{0.25}$ mgA | $Q_1 \leq$ 500 $Q_1$ mgA | $Q_2 \leq$ 1000 $Q_2$ mgA | $Q_4 \leq$ 1500 $Q_4$ mgA | $Q_6 \leq$ 2000 $Q_6$ mgA | Initial Dose Tested mgAm |
|---|---|---|---|---|---|---|---|
| | In Vitro Sustained Release Dissolution Criteria | | | | | | |
| 8C (280 μm) | 22..7 1.6 Opadry ® | — | 110 | 141 | 188 | 214 | 226 |
| 8D (310 μm) | 27.1 | — | 104 | 212 | 257 | 265 | 272 |
| 8E (315 μm) | 25.1 | — | 45 | 74 | 116 | 138 | 250 |
| 8F (335 μm) | 30.9 | — | — | 45 | — | 119 | 180 |
| 8G (400 μm) | 35.6 0.7 Opadry ® | — | — | 32 | — | 77 | 166 |

[1]Examples 8B, 8C and 8G have a water soluble Opadry ® protective coating added over the Surelease ® diffusion barrier coating. For the case of Example 8B, a 0.5% Opadry ® coating was done over a 16.6% Surelease ® coating.

EXAMPLE 9

This example illustrates a process for making sustained release azithromycin multiparticulates which release azithromycin at different rates depending on the thickness of a diffusion barrier coating. The process comprised (1) preparing uncoated azithromycin multiparticulate cores; and (2) applying a diffusion barrier coating over the cores. This example further evaluates the release profile of the multiparticulates.

Azithromycin-containing multiparticulate cores were prepared using a fluid bed processor with rotor insert (Glatt GPCG-5 by Glatt Air Techniques, Ramsey, N.J.). The rotor bowl was initially charged with 2,500 g of azithromycin drug and plasticized hydroxypropyl methylcellulose (Opadry®) binder solution (10% solids concentration) was tangentially sprayed into the rotating bed until an average core granule size of about 250 μm was achieved. Next, a plasticized ethylcellulose (Surelease®) coating suspension diluted to 15% solids was sprayed onto the core particles. A first batch of coated particles was made with a 40% coat. A second batch was then made with a 50% coat.

Finished sustained release beads were tested using the in vitro sustained release dosage test procedure previously described and the results are presented in Table 9-1. Examples 9A and 9B are sustained release embodiments of this invention.

TABLE 9-1

| | In Vitro Sustained Release Dosage Test Dissolution Criteria | $Q_{0.25} \leq$ 200 $Q_{0.25}$ mgA | $Q_1 \leq$ 500 $Q_1$ mgA | $Q_2 \leq$ 1,000 $Q_2$ mgA | $Q_4 \leq$ 1,500 $Q_4$ mgA | $Q_6 \leq$ 2,000 $Q_6$ mgA | Initial Dose Tested mgAm |
|---|---|---|---|---|---|---|---|
| Example | Surelease ® Coating (%) | | | | | | |
| 9A | 40 | 55 | 221 | 401 | 759 | 826 | 1000 |
| 9B | 50 | 11 | 43 | 120 | 275 | 382 | 1000 |

EXAMPLE 10

This example illustrates using the sustained release dissolution criteria in conjunction with in vitro dissolution test results to design a dosage form which exhibits a desired release profile.

As in Example 5, the data of Example 9 were employed in conjunction with the temporal criterion to calculate the maximum scaled mgAm, corresponding to both Example 9A and 9B, which should be used lo make a dosage form according to the invention. Table 10-1 summarizes the maximum scaled dose for Examples 9A and 9B.

TABLE 10-1

Maximum Scaled Dose

| | Maximum Scaled Dose at Sustained Release Multiparticulate |
|---|---|
| 9A | 1,976 mgA |
| 9B | 5,238 mgA |

EXAMPLE 11

This example illustrates using weight criteria in conjunction with in vitro test results to custom design a dosage form tailored for an animal of a given body weight.

The data from Examples 9A and 9B were employed to calculate, as in Example 6, the maximum dose which should be administered to a 100 kg animal. Table 11-1 lists the maximum amounts of sustained release multiparticulate for Examples 9A and 9B which should be employed for a given body weight of 100 kg according to the dissolution criteria and body weight criteria to made a multiparticulate dosage form within the scope of the invention.

TABLE 11-1

Maximum Dose Deliverable To A Given Body Weight

| Example | Maximum Dose Sustained Release Multiparticulate 100 kg Body Weight |
|---|---|
| 9A | 3,953 mgA |
| 9B | 10,471 mgA |

EXAMPLE 12

This example illustrates using the weight criteria in conjunction with in vitro dissolution test results to determine the minimum animal body weight with which a sustained release dosage form should be used.

The minimum weights were calculated in the same manner as for Example 7. Table 12-1 summarizes the minimum body weight for 250 mgAm and 1,000 mgAm total doses of Examples 9A and 9D.

TABLE 12-1

Minimum Body Weight At Given Dose

| Example | Minimum Body Weight per 250 mgA Sustained Release Multiparticulate | Minimum Body Weight per 1,000 mgA Sustained Release Multiparticulate |
|---|---|---|
| 9A | 6.3 kg | 25.3 kg |
| 9B | 2.4 kg | 9.6 kg |

EXAMPLE 13

This example illustrates a process for making sustained release azithromycin multiparticulate in the form of a phase inversion membrane-moderated reservoir system. The process comprised applying directly to azithromycin-containing-multiparticulate a phase inversion membrane coating. This example further evaluates the release profile of the sustained release multiparticulate.

Azithromycin-containing multiparticulate were prepared by loading 1,000 g azithromycin-containing particles directly into a rotary granulator/coater (Freund CF-360 granulator). The rotating particle bed was sprayed with a solution containing 7.5% ethylcellulose (Dow Ethocel S-10, Dow Chemical, Midland, Mich.), 2.5% polyethylene glycol (PEG 3350), 10% isopropanol, 22% ethanol, 54% acetone and 4% water. When 300 g of coating solution solids had been applied to the 1,000 g initial charge, a sustained release multiparticulate was formed with a mean particle size of about 450 μm.

Finished sustained release multiparticulate was tested using the in vitro sustained release dosage test procedure. The results are presented in Table 13-1. Example 13A satisfies the in vitro release criteria and is a sustained release embodiment of the invention.

TABLE 13-1

| Example | Surelease ® Coating (%) | In Vitro Sustained Release Dissolution Criteria $Q_{0.25}$ (mgA) | $Q_1 \leq$ 500 $Q_1$ mgA | $Q_2 \leq$ 1,000 $Q_2$ mgA | $Q_4 \leq$ 1,500 $Q_4$ mgA | $Q_6 \leq$ 2,000 $Q_6$ mgA | Initial Dose Tested mgAm |
|---|---|---|---|---|---|---|---|
| 13A | 23.1 | — | — | 160 | — | 238 | 250 mgA Capsule |

EXAMPLE 14

This example illustrates a process for making sustained release azithromycin hydrophilic matrix tablets which release azithromycin at different rates depending on their composition. The process comprised (1) blending all components except for magnesium stearate; (2) screening and reblending the same components; (3) adding and blending magnesium stearate; and (4) compressing the final blend into tablets.

In batch sizes of 150 grams, azithromycin was shaken for about 15 minutes in a suitably large jar with all other components except magnesium stearate using a Turbula shaker system (Basel, Switzerland). Next, the blend was passed through a 40 mesh sieve and shaken again for ten minutes. Then, magnesium stearate was added and the blend was shaken for five minutes. Using a Manesty type F press (Manesty Machines, Liverpool, England), the final blend was compressed into tablets using either $^{13}/_{32}$ inch standard, round concave (SRC) punches for Examples 14A through 14I or ¾ inch standard round flat punches for Examples 14J and 14K. A summary of compositions of Examples 14A through 14K is shown in Table 14-1.

TABLE 14-1

Sustained Release Hydrophilic Matrix Tablet Compositions

| Example | % Azithromycin Compound | % Lactose | % HPMC[1] | % PVP[2] | % Microcrystalline Cellulose[3] | % Magnesium Stearate |
|---|---|---|---|---|---|---|
| 14A | 54 | 15 | 30 | — | — | 1 |
| 14B | 54 | 20 | 25 | — | — | 1 |
| 14C | 54 | 24.5 | 20 | — | — | 1.5 |
| 14D | 54 | 29.5 | 15 | — | — | 1.5 |
| 14E | 54 | 34.5 | 10 | — | — | 1.5 |
| 14F | 70 | — | 28.5 | — | — | 1.5 |
| 14G | 70 | — | 15 | 13.5 | — | 1.5 |
| 14H | 70 | — | 20 | 8.5 | — | 1.5 |
| 14I | 70 | — | 15 | — | 13.5 | 1.5 |
| 14J | 70 | — | 15 | 13.5 | — | 1.5 |
| 14K | 70 | — | 15 | — | 13.5 | 1.5 |

[1]HPMC means hydroxypropyl methylcellulose. All Examples used Dow Methocel K4M-CR (Dow Chemical, Midland, MI)
[2]PVP means polyvinylpyrrolidone. Kolloidon 17 (BASF Corp., Parsippany NJ)
[3]Microcrystalline Cellulose that was used was Avicel ® PH-102 (FMC Corp.)

Finished sustained release tablets were tested using the in vitro sustained release dosage test procedure and the results are presented in Table 14-2. Examples 14A through 14K satisfy the dissolution criteria and are sustained release embodiments of this invention.

TABLE 14-2

Sustained Release Hydrophilic Matrix Tablet Compositions

| Example | In Vitro Sustained Release Dissolution Criteria $Q_{0.25} \leq$ 200 $Q_{0.25}$ (mgA) | $Q_1 \leq$ 500 $Q_1$ (mgA) | $Q_2 \leq$ 1,000 $Q_2$ (mgA) | $Q_4 \leq$ 1,500 $Q_4$ (mgA) | $Q_6 \leq$ 2,000 $Q_6$ (mgA) | Initial Dose Tested |
|---|---|---|---|---|---|---|
| 8A | — | 37 | — | 69 | 85 | Tablet 250 mgAm |
| 8B | — | 42 | — | 92 | 111 | Tablet 250 mgAm |
| 8C | — | — | 69 | 105 | 124 | Tablet 250 mgAm |
| 8D | — | — | 113 | 158 | 200 | Tablet 250 mgAm |
| 8E | — | 148 | 175 | 236 | 249 | Tablet 250 mgAm |
| 8F | — | — | 52 | — | 94 | Tablet 250 mgAm |

TABLE 14-2-continued

Sustained Release Hydrophilic Matrix Tablet Compositions

| In Vitro Sustained Release Dissolution Criteria Example | $Q_{0.25} \leq 200$ $Q_{0.25}$ (mgA) | $Q_1 \leq 500$ $Q_1$ (mgA) | $Q_2 \leq 1,000$ $Q_2$ (mgA) | $Q_4 \leq 1,500$ $Q_4$ (mgA) | $Q_6 \leq 2,000$ $Q_6$ (mgA) | Initial Dose Tested |
|---|---|---|---|---|---|---|
| 8G | — | — | 51 | — | 91 | Tablet 250 mgAm |
| 8H | — | — | 167 | 218 | 233 | Tablet 250 mgAm |
| 8I | — | — | 109 | 135 | 150 | Tablet 250 mgAm |
| 8J | 80 | 201 | 276 | 413 | 481 | Tablet 1000 mgAm |
| 8K | 88 | 144 | 183 | 245 | 290 | Tablet 1000 mgAm |

EXAMPLE 15

This example illustrates a process for making multiparticulates for use in making delayed-release dosage forms designed to release azithromycin predominantly below the duodenum. The process comprised (1) preparing uncoated azithromycin multiparticulate cores; (2) applying a first, sustained-release coating over the cores; and (3) applying a second pH-sensitive, delayed-release coating over the first coat. This example further illustrates the in vitro delayed release dosage test procedure for evaluating dissolution of the dosage form and release of azithromycin.

Multiparticulate cores containing drug were prepared using a fluid bed processor with rotor insert (Model GPCG-5). The rotor bowl was initially charged with 2,500 g of azithromycin and plasticized hydroxypropyl methylcellulose (Opadry®) binder solution (10% solids concentration) was sprayed into the rotating bed until an average core granule size of about 250 µm was achieved. Next, a plasticized ethylcellulose (Surelease®) coating suspension diluted to 15% solids was sprayed onto the core particles. A first batch of coated particles was made with a total 30% coating. A second batch was then made with a 40% coating. Lastly, both batches of multiparticulate were coated with a delayed-release coating in a fluid bed rotor processor (Glatt Model GPCG-1) until a desired coating end point (indicated in % in Table 15-1) was achieved. The delayed-release coating was a suspension containing 12.3% methacrylic acid copolymers (Eudragit® L 30 D-55), 6.2% talc, 1.5% triethyl citrate and 80% water. For the first batch that had been coated with a 40% Surelease® coat, a 20% delayed release overcoat was applied. For the second batch that had been coated with a 30% Surelease® coat, a 33.7% delayed release overcoat was applied. The final product was delayed-release multiparticulate with particles having an average size of about 300 µm.

The in vitro delayed release dissolution results are presented in Table 15-1 and include the dissolution test criteria. Example 15A is a comparative example of an immediate release capsule that is outside the criteria and scope of the invention. Examples 15B and 15C are delayed-release embodiments made with multiparticulate of these examples.

TABLE 15-1

| Example | In Vitro Delayed Release Dosage Test Dissolution Criteria<br>Formulation Composition, (%) | $Q_{0.25} \leq 10\%$ $Q_{0.25}$ (Acid Stage) | $Q_{0.5} \leq Q_{0.25} + 10\%$ $Q_{0.5}$ (Buffer Stage) | Initial Dose (mg-Am) |
|---|---|---|---|---|
| 15A | Immediate-Release Capsule | 81% | 98% | 250 |
| 15B | Sustained + Delayed-Release Multiparticulate<br>43.6% azithromycin<br>4.4% Opadry ® Solids<br>32.0% Surelease ® Solids<br>12.3% Eudragit ® Solids<br>6.2% Talc<br>1.5% Triethyl Citrate | 0.6% | 0.7% | 250 |
| 15C | Sustained + Delayed-Release Multiparticulate<br>42.2% azithromycin<br>4.2% Opadry ® Solids<br>19.9% Surelease ® Solids<br>20.8% Eudragit ® Solids<br>10.4% Talc<br>2.5% Triethyl Citrate | 0.5% | 6.2% | 250 |

EXAMPLE 16

This example illustrates a process for making sustained release azithromycin hydrophilic matrix tablets which release azithromycin at different rates depending on the extent of surface coating coverage by an aqueous insoluble polymeric barrier material as well as the composition of the hydrophilic matrix tablet core.

Tablet cores were made first by shaking (Turbula System) in a suitable size jar for about 15 minutes the following: 105 g azithromycin, 15 g. hydroxypropyl methylcellulose (HPMC, Dow Methocel® E4M-CR) and 27.75 g microcrystalline cellulose (Avicel PH-102, FMC Corp.). The resulting blend was then passed through a 40 mesh sieve and shaken for ten additional minutes. Then, 2.25 g of magnesium stearate was added and the mixture was shaken for five minutes. Using a Manesty type F press fitted with 13/32 inch standard round concave (SRC) punches, the final blend was compressed into tablet cores.

Next, the insoluble polymeric barrier material was prepared by adding 159 g HPMC (Dow Methocel® K100LV premium CR) to a Hobart mixer. While mixing at medium speed, 27 g castor oil was slowly added and the mixing was continued 15 minutes. An ethylcellulose solution was prepared in a separate container by slowly adding 10 g ethylcellulose (Dow Ethocel® S10) to 190 ethanol while stirring. After the ethylcellulose went into solution, the 200 g of ethylcellulose solution was slowly added to the Hobart and the contents were mixed for 15 minutes. The resultant wet mass was spread out on a polyethylene lined tray and dried in a forced hot air dryer at 50° C. for four hours. After drying, 78 g of the dried mass was forced through a 25 mesh sieve and collected in a jar. Magnesium stearate (2 g) and colloidal silicon dioxide (1 g) were added to the jar and the jar was shaken for five minutes.

Using a Manesty type F press and 13/32 inch standard round concave (SRC) punches, the polymeric barrier material was compressed in a variety of configurations over the matrix tablet cores. In one configuration, the core was placed in the punch and various amounts of polymeric barrier material were compressed on top of the matrix tablet core.

Finished tablets produced in this way had a polymeric barrier coat on the top of the matrix tablet core. In a second configuration, different amounts of polymeric barrier material were placed in the die of the punch underneath the matrix core as well as on top of the matrix core and the composite was compressed into final tablets. Finished tablets produced in this second way had a polymeric barrier coat on both the top and bottom surfaces of the matrix table core.

In another process for making polymeric barrier coated hydrophilic matrix tablets, an adhesive polymer (Epoxi-Patch, Hysol Corp. Olean, N.Y.) was used as the polymeric barrier material and was applied to various surfaces of the matrix tablet cores. Polymeric barrier coatings were not only : applied to the top and/or bottom surfaces of the matrix tablet core, but also around the sides of the tablet.

EXAMPLE 17

This example illustrates a process for making delayed release azithromycin hydrophilic matrix tablets which are designed to release azithromycin predominantly below the duodenum.

Tablet cores were made first by shaking (Turbula System) for about 15 minutes in a jar 105 g azithromycin, 15 g. hydroxypropyl methylcellulose (HPMC, Dow Methocel® E4M-CR) and 27.75 g microcrystalline cellulose (Avicel PH-102, FMC Corp.). This blend was then passed through a 40 mesh sieve and shaken for ten minutes. Then, 2.25 g of magnesium stearate was added and the mixture was shaken for five minutes. Using a Manesty type F press fitted with 13/32 inch standard round concave (SRC) punches, the final blend was compressed into tablet cores.

A delayed-release coating suspension containing 12.3% methacrylic acid copolymers (Eudragit® L 30 D-55), 6.2% talc; 1.5% triethyl citrate and 80% water was prepared and applied as a 10% coating, using an HCT-30 Hi-Coater (Vector-Freund) to spray the solution onto the matrix tablet cores. Because the coating is soluble in environments where the pH is greater than 5.5, the tablets thus prepared release azithromycin from the hydrophilic matrix tablet cores below the stomach where the pH is greater than 5.5, and the cores do so in a sustained manner that delivers azithromycin predominantly below the duodenum.

EXAMPLE 18

This example illustrates a process for making an osmotic azithromycin sustained release tablet with a bilayer (two compartment) core surrounded by a semipermeable membrane with a passage through its surface. One tablet core layer has an osmotically effective composition containing azithromycin and the second tablet core layer contains an expanding hydrogel.

The first tablet core layer material was prepared by Turbula blending for about 15 minutes 70 g polyethylene oxide having a molecular weight of 5,000,000 (Polyox® Coagulant), 23 g sodium chloride and 5 g hydroxypropyl methylcellulose (Dow Methocel® E4M) in a jar. The contents were passed through a 60 mesh sieve and collected in a jar. Then, 2 g of magnesium stearate were added and the mixture Turbula blended for 5 minutes.

The second tablet core layer material containing azithromycin was prepared by Turbula blending for about 15 minutes 50 g azithromycin, 150 g polyethylene oxide having a Molecular weight of 100,000 (Polyox® N-20, Union Carbide Corp., Danbury, Conn.) and 10 g hydroxypropyl methylcellulose (Dow Methocel® E4M) in a jar. The contents were passed through a 60 mesh sieve and collected in a jar. Then, 4 g of magnesium stearate were added and the mixture Turbula blended for 5 minutes.

To make a bilayer tablet core, a Manesty type F press with 13/32 inch standard round concave (SRC) punches was used. First, the first tablet core layer material was partially compressed in the punch. Then, the second tablet core layer material containing azithromycin was filled on top of the first layer and full compression was applied to form bilayer tablet cores.

A coating solution was prepared with 68% methylene chloride, 28.5% methanol, 3.3% cellulose acetate (Eastman CA-398-10) and 1.7% polyethylene glycol 3350. An HCT-30 Hi-Coater (Vector-Freund) was used to spray the coating solution onto the bilayer tablet cores. Sufficient coating was applied to form a wall around the tablet core of about 0.006 inch thickness. After coating, the coater rotation was reduced and the cores were dried for five minutes. The coating forms a semipermeable barrier wall around the tablet core which is permeable to water and impermeable to azithromycin and other tablet core excipients.

A 0.5 mm hole was mechanically drilled through the coating to expose the azithromycin-containing layer to the use environment.

EXAMPLE 19

This example illustrates a process for making an osmotic azithromycin sustained release tablet which was designed with a core containing an osmotically effective composition surrounded by a semipermeable membrane with a passage through its surface.

Tablet cores were made first by Turbula blending for about 10 minutes in a jar 30 g azithromycin fumarate with 70 g lactose. The contents were passed through a 40 mesh sieve and collected in the jar. Then, 2 g magnesium stearate were added and the mixture Turbula blended for 5 minutes. Using a Manesty type F press, the final blend was compressed into tablet cores using 13/32 inch standard round concave (SRC) punches.

A coating solution was prepared with 68% methylene chloride, 28.5% methanol, 3.3% cellulose acetate (Eastman CA-398-10) and 0.2% polyethylene glycol 3350. An HCT-30 Hi-Coater (Vector-Freund) was used to spray the coating solution onto the tablet cores. Sufficient coating was applied to form a wall around the tablet core of about 0.006 inch thickness. After coating, the coater rotation was reduced and the cores were dried for five minutes. The coating forms a semipermeable barrier wall around the tablet core which is permeable to water and impermeable to azithromycin and other tablet core excipients.

Next, different diameter passageways from 0.008 inch to 0.020 inch diameter were mechanically drilled through the top of the semipermeable wall connecting the exterior of the tablet with the tablet core containing the azithromycin.

EXAMPLE 20

This example illustrates a process for making multiparticulates for use in making delayed-release dosage forms designed to release azithromycin predominantly below the duodenum. The process comprises (1) preparing uncoated azithromycin multiparticulate cores; (2) applying a first, sustained-release diffusion barrier coating over the cores; and (3) applying a second, pH-sensitive, delayed release coating over the first coat.

Azithromycin-containing multiparticulate cores are prepared by blending azithromycin compound with microcrystalline cellulose (Avicel® PH101, FMC Corp., Philadelphia, Pa.) in relative amounts of 95.5 (w/w), wet massing the blend in a Hobart mixer with water equivalent to approximately 27% of the weight of the blend, extruding the wet mass through a perforated plate (Luwa EXKS-1 extruder, Fuji Paudal Co., Osaka Japan), spheronizihg the extrudate (Luwa QJ-230 marumerizer, Fuji Paudal Co.) and drying the final cores which are about 1 mm diameter.

Next, a Wurster bottom spray fluid bed processor (Glatt GPCG-1) is used to coat the uncoated azithromycin-containing multiparticulate with a diffusion barrier coating. A plasticized ethylcellulose (Surelease®) coating suspension diluted to 15% solids is sprayed onto the core particles. Typically, a 5% to 20% diffusion barrier coating is applied. The amount of barrier coating applied determines the rate of azithromycin release from the uncoated core.

Last, a Wurster bottom spray fluid bed processor (Glatt GPCG-1) is used to apply a delayed release coating over the diffusion barrier coated particles. Typical delayed release coating levels are 25% to 50% in order to be sure that the delayed release dissolution criterion are met. The delayed-release coating is a suspension containing 12.3% methacrylic acid copolymers (Eudragit® L 30 D-55), 6.2% talc, 1.5% triethyl citrate and 80% water.

Because the delayed release coating is soluble in environments where the pH is greater than 5.5, the multiparticulates thus prepared release azithromycin from the barrier coated particle cores below the stomach where the pH is greater than 5.5, and the particle cores do so in a sustained manner that delivers azithromycin predominantly below the duodenum.

EXAMPLE 21

This example illustrates a process for making multiparticulates for use in making delayed-release dosage forms designed to release azithromycin predominantly below the duodenum. The process comprises (1) preparing uncoated azithromycin multiparticulate cores; (2) applying a protective coat over the core particles; and (3) applying a second, pH-sensitive, delayed release coating over the first coat.

Multiparticulate cores containing drug are prepared using a fluid bed processor with rotor insert (Model GPCG-1). The rotor bowl is initially charged with 400 g of azithromycin drug and a binder solution containing 5% poly(ethyl acrylate, methyl acrylate)(Eudragit NE-30-D), 5% plasticized hydroxypropyl methylcellulose (Opadry®) and 90% water is sprayed into the rotating bed until an average core granule size of about 250 μm was achieved.

Onto the uncoated core particles in the same fluid bed processor with rotor insert, a binder solution containing 5% plasticized hydroxypropyl methylcellulose (Opadry®) solution is sprayed until a coating of 10% is applied This intermediate coating enhances the adhesion to the core particles of the final delayed release coating.

A delayed release coating (typically 15% to 50% is required to meet the delayed release criterion) is applied using the same fluid bed processor as above. The delayed-release coating is a suspension containing 12.3% methacrylic acid copolymers (Eudragit® L 30 D-55), 6.2% talc, 1.5% triethyl citrate and 80% water. The final product is a delayed-release multiparticulate with particles having an average size of about 300 μm.

EXAMPLE 22

This example illustrates the preparation of azithromycin bead cores and coating them with a controlled-release coating. The coating can be applied in conventional equipment. The rate of release of drug from the coated beads is dependent on the amount of coating applied.

Drug-containing beads are prepared by blending azithromycin fumarate with microcrystalline cellulose (Avicel® CL 611. FMC) in relative amounts of 95:5, wet-massing the blend in a Hobart mixer with water until a dough is obtained, extruding the wet mass through a perforated plate (Luwa extruder) and spheronizing the extrudate (Luwa spheronizer). The beads so prepared are dried and coated in an Aeromatic Strea-1 benchtop Wurster coater (batch size 100 g). The coating solution is prepared by dissolving 36 g cellulose acetate (Eastman CA 398-10), 7.9 g poly(ethylene glycol) (PEG 400), and the required amount of sorbitol in a mixture of methylene chloride, methanol and water (15:10:1) sufficient to bring the polymer concentration to about 2%. The coating is applied in the fluidized bed until the desired thickness is obtained. The following compositions give sustained-release of azithromycin:

| Sorbitol In Coating Solution | coating thickness |
| --- | --- |
| 3 g | 0.01 cm |
| 3 g | 0.02 cm |
| 3 g | 0.05 cm |
| 3 g | 0.10 cm |
| 6 g | 0.01 cm |
| 6 g | 0.02 cm |
| 6 g | 0.05 cm |
| 6 g | 0.10 cm |
| 12 g | 0.01 cm |
| 12 g | 0.02 cm |
| 12 g | 0.05 cm |
| 12 g | 0.10 cm |

EXAMPLE 23

This example illustration of tablets coated with a membrane which develops pores when placed in a use environment for sustained release of azithromycin.

Oval-shaped tablets containing 750 mg azithromycin fumarate, 100 mg sorbitol and 10 mg magnesium stearate are prepared by compressing a mixture of the powders on a Carver Press. The tablets are placed in a pan coater and coated with a polymer solution containing cellulose acetate (Eastman CA 383-40) and poly(ethylene glycol) (PEG 400) in acetone, to which has been added impalpable lactose to give a ratio of CA:PEG:lactose of 40:40:20 and a total solids content of 50 g/l. The coating process is continued until the tablets have received the desired amount of coating. Coatings equivalent to 10%, 15%, 20%, 25%, and 30% of the tablet weight give successive decreases in the rate of azithromycin release.

EXAMPLE 24

This example illustrates the preparation of perforated coated tablets with a coating of ethylcellulose which deliver azithromycin from a central hole.

Tablets containing 750 mg azithromycin fumarate and 100 mg hydroxypropylmethylcellulose (Dow Methocel K100LV) are prepared by compressing a mixture of the powders on a Carver, press using a standard round die and round flat-faced punches of 1.3 cm diameter. The tablets are coated in a pan coater with a solution containing 10% ethylcellulose (Dow EC S-10) in acetone and ethanol until the applied coating reaches 20% of the tablet weight. The coated tablets are removed from the coater and further dried at 50° C. overnight. A 2 mm hole is then drilled through the center of each tablet to yield a sustained release dosage form.

EXAMPLE 25

This example illustrates the preparation of perforated coated tablets with a cellulose acetate coating which deliver azithromycin from a central hole.

Tablets containing 750 mg azithromycin fumarate and 100 mg hydroxypropylmethylcellulose (Dow Methocel K100LV) are prepared by compressing a mixture of the powders on a Carver press using a standard round die and round flat-faced punches of 1.3 cm diameter. The tablets are coated in a pan coater with a solution containing 10% cellulose acetate (Eastman 398-10) in acetone until the the applied coating reaches 20% of the tablet weight. The coated tablets are removed from the coater and further dried at 50° C. overnight. A 2 mm hole is then drilled through the center of each tablet to yield a sustained release dosage form.

EXAMPLE 26

This example illustrates the preparation of perforated coated tablets with a copolymeric ethylene/vinyl acetate coating which deliver azithromycin from a central hole.

Tablets containing 750 mg azithromycin fumarate and 100 mg hydroxypropylmethylcellulose (Dow Methocel K100LV) are prepared by compressing a mixture of the powders on a Carver press using a standard round die and round flat-faced punches of 1.3 cm diameter. The tablets are coated by dipping into a solution containing 10% ethylene vinyl acetate (Aldrich Chemical Co.) in methylene chloride. The coated tablets are further dried at 50° C. overnight. A 2 mm hole is then drilled through the center of each tablet to yield a sustained release dosage form.

EXAMPLE 27

This example illustrates preparation of perforated coated tablets which utilize a geometric approach to linearizing the release of azithromycin.

Tablets are prepared as in Example 26, except that conical punches are used to give a tablet increasing in thickness from the center outward at an angle of 30°. These tablets are completely coated by dipping into a solution of 20% cellulose acetate (Eastman CA 398-10) in acetone. The tablets are allowed to air dry, then are dried at 50° overnight. As before, a 1 mm hole is drilled through the center of the tablet to yield a sustained-release dosage form

EXAMPLE 28

This example illustrates preparation of hemispherical pellets having a hole in the center of the flat face.

Azithromycin dihydrate and polyethylene (PEP-315, Union Carbide) powder are each passed through a 60 mesh screen before use. The following blends are prepared:

| Azithromycin | Polyethylene |
|---|---|
| 3 g | 7 g |
| 4 g | 6 g |
| 5 g | 5 g |
| 6 g | 4 g |
| 7 g | 3 g |

Each blend is prepared by mixing the powders for 5 minutes in a Turbula mixer. An aliquot of each blend is then placed into a metal mold in the form of a hollow cylinder having a round bottom. The radius of curvature of the bottom of the mold is equal to that of the cylindrical section. (The mold is split into two halves along the axis of the cylinder, to allow removal of the compact.) Two different-sized molds are used to yield different doses: A mold with radius of 0.5 cm is charged with 260 mg of blend, yielding pellets containing 78, 104, 130, 156, and 182 mg of drug, for the blends described above. A mold with radius of 1.0 cm is charged with 2100 mg of blend, yielding pellets containing 630, 840, 1050, 1260, and 1470 mg of drug, for the blends described above. The loaded mold is placed in an oven at 150° C. for 30 min. After heating, the blends are compressed in the mold by inserting a tight-fitting metal plunger. The plunger is removed and the mold allowed to cool for 20 min at room temperature. The mold is disassembled and the hemispheric drug containing pellets are removed and trimmed with a scalpel to remove any irregular edges. The hemispheric pellets are placed face-down in a dish and covered with molten paraffin. The resulting block of paraffin is removed and cut into sections, each section containing one pellet. The exposed face of each pellet is further coated with molten paraffin. After the paraffin coating is solidified, a hole is drilled through the coating in the center of the flat face of the hemisphere. The resulting hemispherical pellets exhibit sustained-release of azithromycin. These pellets are usable as-is, or several pellets can be placed into gelatin capsules to form higher-dose units for dosing to humans or animals. Four of the 1 cm radius pellets of this example, containing 1470 mg of azithromycin each, are placed in a capsule of 2 cm inside diameter and 4 cm length to make a capsule containing 5880 mg azithromycin.

EXAMPLE 29

This example illustrates the preparation of coated cylindrical tablets or boluses which deliver azithromycin through slits cut in the periphery of the coating.

A blend of azithromycin is prepared with 10% HPMC and 2%. magnesium stearate and compression-molded into cylinders of 1 cm and 2 cm diameter. The length of the cylinders is dependent on the amount of blend charged into the mold, as shown in the table below:

| diameter | amt of blend | amt of azithromycin | length |
|---|---|---|---|
| 1 cm | 1 g | 880 mg | 1.3 cm (approx) |
| 1 cm | 2 g | 1760 mg | 2.6 cm |
| 1 cm | 3 g | 2640 mg | 3.9 cm |
| 2 cm | 3 g | 2640 mg | 0.84 cm |

-continued

| diameter | amt of blend | amt of azithromycin | length |
|---|---|---|---|
| 2 cm | 6 g | 5280 mg | 1.7 cm |
| 2 cm | 12 g | 10560 mg | 3.4 cm |

The cylinders so prepared are thoroughly coated with ethylcellulose (Dow EC S-100) by dipping into a solution of 20% EC in acetone and dried at 50° C. overnight. A sharp blade is then used to cut four equidistant longitudinal slits, approximately 0.5 mm wide, along the periphery of each cylinder to yield sustained-release dosage forms. These larger dosage forms are especially useful for treatment of animals, especially ruminants, which can retain the dosage forms in the rumen for a prolonged period of time.

EXAMPLE 30

This example illustrates the preparation of a delivery system consisting of a porous hydrophobic membrane capsule with an osmotic "push" compartment to drive a piston acting on any dispensable azithromycin drug composition.

A porous hydrophobic membrane capsule is prepared by the following procedure:

First glucose is milled to a 230 mesh screen size. The milled glucose (15 g is then mixed with poly(d,l-lactide) (35 g, 200,000 avg. mol. wt.) and the mixture is blended and milled. A quantity (1.15 g) of the resulting particles is then placed in a transfer mold where the particles are molded in the form of a membrane cup with an open end. The dimensions of the membrane cup are 2.6 cm in length, with an inside diameter of 0.457 cm and a wall thickness of 0.06–0.08 cm. The membrane cup is placed in water and at 37° C. for 14 days. The water is changed after 3,7, and 10 days. The membrane cup is then cleaned with 70% ethanol/30% water, followed by water and dried under vacuum.

Next, sodium chloride is milled to 230 mesh. To the milled sodium chloride (6 g) is added sodium carboxymethylcellulose (4 g); and the mixture is blended to produce a uniform osmotically effective composition. The composition is pressed into osmotically effective tablets at a pressure of 1000 lb to produce a 100 mg cylindrical tablet with one flat and one convex end, and with a diameter of about 0.457 cm to conform to the inner shape of the membrane cup.

An inert spacer or piston is formed by combining ultrathene (0.5 g) and vynathene (0.5 g) and placing the mixture in a transfer mold shaped to provide a piston to fit in the membrane cup.

The sodium chloride tablet is placed into the hydrophobic membrane capsule. The piston is inserted into the capsule on top of the sodium chloride tablet. A dispensable azithromycin composition (such as a slurry of azithromycin in poly(ethylene glycol) or another suspending agent) is then filled on top of the piston. Lastly, the device is sealed with a cap which is equipped with a hole for dispensing the drug. When placed in an aqueous environment, device imbibes water by osmosis. This osmotic imbibition drives the piston, which in turn acts on the azithromycin composition, forcing it out the hole in the cap at a controlled rate.

EXAMPLE 31

This example illustrates the preparation of a pH-Dependent Coated Tablet with a Cellulose Acetate Phthalate Coat Azithromycin tablet cores are manufactured according to the formula described in Table 31-1. Tablet cores are prepared by wet granulation of all tablet ingredients (except magnesium stearate/sodium lauryl sulfate). The dried granules are blended with the lubricant mixture magnesium stearate/sodium lauryl sulfate, followed by tableting on a tablet press. Tablet cores are then spray-coated with an acetone solution of cellulose acetate phthalate (CAP) in a HCT-60 Hi-Coaters spray-coating apparatus (Freund Ind. Corp., Tokyo). The CAP is plasticized with 25% (by weight) diethylphthalate (DEP). Sufficient CAP is sprayed onto the tablets to result in a final coating polymer weight, after drying, of 20 wt %, relative to the weight of the uncoated tablet bed.

TABLE 31-1

Azithromycin Tablet Core Formulation

| COMPONENT | WEIGHT (MG/TABLET) |
|---|---|
| Azithromycin dihydrate* | 524.10 |
| Pregelatinized starch** | 54.00 |
| Calcium phosphate dibasic, anhydrous | 277.68 |
| Sodium croscarmellose# | 18.00 |
| Magnesium stearate/Sodium lauryl sulfate (90/10) | 26.22 |
| TOTAL | 900 |

*Based on a theoretical potency of 95.4%.
**Starch 1500
Ac-Di-Sol (FMC Corp.).

EXAMPLE 32

This example illustrate the preparation of a pH-Dependent CAP-Coated Tablet with Barrier Coat.

Azithromycin tablets are manufactured as described in Example 31. Tablets are spray coated with a solution of hydroxypropylmethylcellulose (HPMC; Colorcon, Inc.) in water, using a HCT-60 Hi-Coater. In this manner, tablets are coated with a 5 wt % barrier coat of HPMC, relative to the initial tablet weight. Tablets are then further spray-coated with cellulose acetate phthalate (CAP) and DEP plasticizer (as described in Example 31), in the HCT-60 Hi-Coater. Sufficient CAP is sprayed onto the tablets to result in a final coating polymer weight, after drying, of 20 wt %, relative to the weight of the uncoated tablet. The HPMC coat serves as a barrier between azithromycin and the pH-sensitive CAP coat. This barrier coat prevents premature dissolution (or weakening) of the CAP coat, e.g., in the low pH environment of the stomach potentially caused by a locally high pH in the tablet interior due to the presence of azithromycin.

EXAMPLE 33

This example illustrates the preparation of a pH-Dependent Coated Tablet with an Acrylic Resin Coat.

Azithromycin tablets are manufactured according to Example 31. Tablets are then spray-coated with an acrylic resin in an HCT-60 Hi-Coater® spray-coating apparatus (Freund Ind. Corp., Tokyo). The resin consists of a 1:1 (w/w) mixture of Eudragit-L® and Eudragit-S®, which are methacrylic acid/methyl methacrylate copolymers, available from the RöhmPharma Corporation (Darmstadt, Germany). The formula for the spray coating solution is given in Table 33-1. The Eudragit-L/S Primary Layer coating formulation is sprayed on the tablets in the Hi-Coater, followed by spray-coating with the Covering Layer formulation. The total coating polymer weight applied is 15% of the weight of the uncoated tablet bed.

TABLE 33-1

Eudragit ® Spray-Coating Formulation for Tablets

| | PARTS BY WEIGHT |
|---|---|
| PRIMARY LAYER | |
| 1:1 Eudragit-L/S 12.5% soln. | 2000 |
| Dibutylphthalate | 25 |
| Talc | 50 |
| Isopropyl alcohol/acetone | to 4000 |
| COVERING LAYER (COLORED) | |
| 1:1 Eudragit-L/S 12.5% soln. | 1200 |
| Talc | 140 |
| Magnesium stearate | 40 |
| Titanium dioxide | 50 |
| Pigment | 50 |
| PEG-6000 | 20 |
| Water | 40 |
| Isopropyl alcohol/acetone | to 3000 |

EXAMPLE 34

This example illustrates the preparation of a pH-Dependent Acrylic Resin-Coated Tablet with Barrier Coat.

Azithromycin tablets are manufactured according to Example 31. Tablets are spray coated with a solution of hydroxypropylmethylcellulose (HPMC) (Colorcon, Inc.) in water, using a HCT-60 Hi-Coater. In this manner, tablets are coated with a 5 wt % barrier coat of HPMC, relative to the initial tablet weight. Tablets are then spray-coated with an acrylic resin in an HCT-60 Hi-Coater® spray-coating apparatus (Freund Industries Corp, Tokyo). The resin consists of a 1:1 (w/w) mixture of Eudragit-L® and Eudragit-S®, which are methacrylic acid/methyl methacrylate copolymers, provided by the RöhmPharma Corporation (Darmstadt, Germany). The formula for the spray coating solution is given in Table 33-1. The Eudragit-L/S Primary Layer coating formulation is sprayed on the tablets in the Hi-Coater, followed by spray-coating with the Covering Layer formulation. The total acrylic resin polymer weight applied is 15% of the weight of the uncoated tablet bed. The HPMC undercoat serves as a barrier between azithromycin and the pH-sensitive acrylic resin coat. This barrier coat prevents premature dissolution (or weakening) of the acrylic resin coat, e.g., in the low pH environment of the stomach, potentially caused by a locally high pH in the tablet interior due to the presence of azithromycin.

EXAMPLE 35

This example illustrates the preparation of Azithromycin Tablets with a Double Delayed Release Coat.

Azithromycin tablets are manufactured according to Example 31. Tablets are spray coated with an aqueous mixture of ethylcellulose (EC) (Surelease, Colorcon Inc.) and hydroxypropylmethylcellulose (HPMC) (Opadry®; Colorcon Inc.) at 70/30 EC/HPMC, using a HCT-60 Hi-Coater®. In this manner, tablets are coated with a 5 wt % coat of EC/HPMC, relative to the initial tablet weight. Tablets are then spray-coated with an acrylic resin in an HCT-60 Hi-Coater® spray-coating apparatus (Freund Industries Corp., Tokyo). The resin consists of a 1:1 (w/w) mixture of Eudragit-L® and Eudragit-S®, which are meth- acrylic acid/methyl methacrylate copolymers, available from RöhmPharma Corporation (Darmstadt, Germany). The formula for the spray coating solution is given in Table 33-1. The Eudragit-L/S Primary Layer coating formulation is sprayed on the tablets in the Hi-Coater, followed, by spray-coating with the Covering Layer formulation. The total acrylic resin coating polymer weight applied is 10% of the weight of the uncoated tablet bed.

EXAMPLE 36

This example illustrates the preparation of pH-Dependent Coated Beads.

Azithromycin beads are prepared as follows. Azithromycin, microcrystalline cellulose, and water (according to the formula in Table 36-1) are mixed in a Hobart mixer to form a paste. The paste is extruded into strands and spheronized, using a Fuji-Paudal extruder/spheronizer, forming small beads (about 1 mm diam), which are subsequently dried. The beads are subsequently spray-coated with an acrylic resin in a Glatt GPCG-1 Fluid Bed Processor. The resin consists of a 1:1 (w/w) mixture of Eudragit-L® and Eudragit-S®, which are methacrylic acid/methyl methacrylate copolymers, provided by the RöhmPharma Corporation (Darmstadt, Germany). The formula for the coating solutions is presented in Table 33-1. The Eudragit-L/S Primary Layer coating formulation is sprayed on the beads in the fluid bed processor, followed by spray-coating with the Covering Layer formulation. The total coating polymer weight applied is 25% of the weight of the uncoated bead bed.

TABLE 36-1

Formula for Azithromycin beads of Example 36.

| Component | mg/g |
|---|---|
| Azithromycin dihydrate* | 951.61 |
| Microcrystalline cellulose** | 48.39 |
| Water# | 270.00 |
| TOTAL | 1,000.00 |

*Bulk potency 93.0%.
**Avicel PH101
Volatile, substantially removed from final dosage form.

EXAMPLE 37

This example illustrates the preparation of PH-Dependent Coated Beads with an HPMC Barrier Coating.

Azithromycin/microcrystalline cellulose beads were prepared as in Example 36. In a Glatt GPCG-1 Fluid Bed Processor, these beads are coated with an aqueous solution of HPMC (Opadry®, Colorcon, Inc.). The final dry HPMC barrier coat comprises 5% of the weight of the uncoated beads. The HPMC-coated azithromycin beads are then coated with a 25% (by weight) coat of acrylic resin as described in Example 36. The HPMC undercoat serves as a barrier between azithromycin and the pH-sensitive acrylic resin coat. This barrier coat prevents premature dissolution (or weakening) of the acrylic resin coat, e.g., in the low pH environment of the stomach, potentially caused by a locally high pH in the tablet interior due to the presence of azithromycin.

What is claimed is:

1. A controlled release dosage form for oral administration to a human comprising a therapeutically effective amount of azithromycin and one or more additional components, said dosage form controlling the azithromycin release rate into the gastrointestinal tract of said human, thereby decreasing the incidence or severity of gastrointestinal side effects, said dosage form releasing the bulk of its azithromycin in a portion of the gastrointestinal tract distal to the duodenum.

2. The controlled release dosage form of claim 1 that releases 80% or more of the azithromycin in the portion of the gastrointestinal tract distal to the duodenum.

3. The dosage form of claim 2 that release no more than about 10% of the azithromycin in the stomach.

4. The dosage form of claim 2 comprising a plurality of particles, said particles having a diameter of from about 50 micrometers to about 3 millimeters.

5. The dosage form of claim 4 wherein said particles comprise azithromycin and a pharmaceutically acceptable carrier or diluent.

6. The dosage form of claim 3 comprising a plurality of particles, said particles having a diameter of from about 50 micrometers to about 400 micrometers.

7. The dosage form of claim 3 comprising a plurality of particles, said particles having a diameter of from about 50 micrometers to about 3 millimeters.

8. The dosage form of claim 2 in the form of a capsule, a tablet, a suspension or a sachet.

9. The dosage form of claim 4 in the form of a sachet.

10. The dosage form of claim 4 wherein said particles further comprise a matrix material.

11. The dosage form of claim 10 wherein said matrix material is selected from the group consisting of waxes, cellulose and derivatives thereof, polymers; and mixtures thereof.

12. The dosage form of claim 11 further comprising a release-modifying agent.

13. The dosage form of claim 3 comprising a hydrogel.

14. The dosage form of claim 1 or 2 comprising a plurality of particles, said particles having a diameter of from about 50 micrometers to about 3 millimeters and said particles further comprising a core, said core having a first surface coating thereon.

15. The dosage form of claim 14 wherein said core comprises azithromycin and a pharmaceutically acceptable vehicle, carrier or diluent.

16. The dosage form of claim 14 wherein said first surface coating comprises a sustained release coating.

17. The dosage form of claim 14 further comprising a second surface coating on said core.

18. The dosage form of claim 17 wherein said second surface coating comprises a sustained release coating.

19. The dosage form of claim 17 wherein said second surface coating comprises an enteric coating.

20. The dosage form of claim 1 comprising a matrix multiparticulate.

21. The dosage form of claim 20 wherein said matrix multiparticulate comprises a plurality of azithromycin-containing particles, each particle comprising a mixture of azithromycin with one or more excipients, said mixture forming the matrix limiting the release rate of the azithromycin into the gastrointestinal tract.

22. The dosage form of claim 20 wherein said release rate is such that no more than 70% of the azithromycin is released within about one-half hour from time of ingestion.

23. The dosage form of claim 1 wherein the azithromycin is in the form of a pharmaceutically acceptable salt.

24. The dosage form of claim 1 wherein the azithromycin is in an anhydrous form.

25. The dosage form of claim 1 wherein the azithromycin is in a hydrated form.

26. The dosage form of claim 23 wherein the azithromycin is in a dihydrate form.

27. The dosage form of claim 1 wherein said azithromycin is present in an amount of from about 1 gram to about 7 grams.

28. The dosage form of claim 25 wherein said azithromycin is present in an amount of from about 1.5 grams to about 4 grams.

* * * * *